(12) United States Patent
Tsuruhami et al.

(10) Patent No.: US 7,998,721 B2
(45) Date of Patent: Aug. 16, 2011

(54) DIGLYCOSIDASE AND GENE ENCODING THE SAME

(75) Inventors: Kazutaka Tsuruhami, Gifu (JP); Shigeharu Mori, Gifu (JP); Yoshinao Koide, Gifu (JP)

(73) Assignee: Amano Enzyme Inc., Gifu (JP)

( * ) Notice: Subject to any disclaimer, the term of this patent is extended or adjusted under 35 U.S.C. 154(b) by 578 days.

(21) Appl. No.: 11/997,005

(22) PCT Filed: Jul. 27, 2006

(86) PCT No.: PCT/JP2006/314831
§ 371 (c)(1),
(2), (4) Date: Jul. 21, 2008

(87) PCT Pub. No.: WO2007/013539
PCT Pub. Date: Feb. 1, 2007

(65) Prior Publication Data
US 2010/0221810 A1 Sep. 2, 2010

(30) Foreign Application Priority Data
Jul. 29, 2005 (JP) .................................. 2005-219811

(51) Int. Cl.
C12N 9/24 (2006.01)
C12N 1/00 (2006.01)
C12N 15/00 (2006.01)
C07H 21/04 (2006.01)

(52) U.S. Cl. ................. 435/200; 435/254.5; 435/320.1; 536/23.2

(58) Field of Classification Search ........................ None
See application file for complete search history.

(56) References Cited

U.S. PATENT DOCUMENTS

| 7,109,014 B1 * | 9/2006 | Yamamoto et al. | 435/201 |
| 7,118,895 B2 * | 10/2006 | Tsuruhami et al. | 435/125 |
| 2003/0194469 A1 * | 10/2003 | Tsuruhami et al. | 426/52 |
| 2005/0208177 A1 * | 9/2005 | Tsuruhami et al. | 426/15 |

FOREIGN PATENT DOCUMENTS

| JP | 08-140675 | 6/1996 |
| WO | WO 00/18931 | 4/2000 |
| WO | WO 03/087290 | * 10/2003 |

OTHER PUBLICATIONS

Tsuruhami et al., "Isolation and Characterization of a β-Primeberosidase-Like Enzyme from *Penicillium multicolor*" Biosci. Biotechnol. Biochem, 70(3): 691-698 (2006).

* cited by examiner

*Primary Examiner* — Nashaat Nashed
(74) *Attorney, Agent, or Firm* — Occhiuti Rohlicek & Tsao LLP

(57) ABSTRACT

A novel diglycosidase produced by a microorganism belonging to the genus *Penicillium*, having the following physicochemical properties:
(1) action and substrate specificity: it acts on a disaccharide glycoside, releasing the disaccharide sugar and the aglycone thereof;
(2) optimum pH: around 4.5;
(3) pH stability: it is stable at pH 4.0 to 8.0 under the processing condition of 37° C. for 30 minutes, and retains its 80% or more of the activity even after processing at pH 4.0 or lower;
(4) optimum temperature: around 60° C. in a sodium acetate-acetic acid buffer solution (pH 5.5);
(5) thermal stability: it is stable at 50° C. or lower in a sodium acetate-acetic acid buffer solution (pH 5.5) and retains 45% of the activity even after processing at 60° C. for 40 minutes;
(6) molecular weight: 40,000±5,000 Da based on SDS-PAGE measurement; and
(7) isoelectric point (pI): about 4.3.

12 Claims, 7 Drawing Sheets

DIGLYCOSIDASE AND GENE ENCODING THE SAME

CROSS-REFERENCE TO RELATED APPLICATIONS

This application is the National Stage of International Application No. PCT/JP2006/314831, filed on Jul. 27, 2006, which claims the priority of Japanese Application No. 2005-219811, filed on Jul. 29, 2005. The contents of both applications are hereby incorporated by reference in their entirety.

TECHNICAL FIELD

The present invention relates to a novel diglycosidase produced by a microorganism belonging to the genus *Penicillium* that has an enzyme activity by acting on the disaccharide glycoside, releasing the disaccharide sugar and the aglycone, and a gene coding the same.

BACKGROUND ART

Alcoholic fragrances, a group of plant fragrance ingredients, such as geraniol, linalool, benzyl alcohol, (Z)-3-hexenol, 2-phenylethanol, and C13-norterpenoid alcohols, have an important role in fragrance emission from flowers, tea, fruits, wine, and others. Among these fragrance ingredients, geraniol, linalool, and others, which are considered to play an important role in fragrance emission from flowers, have been known to be present as fragrance precursors in the form of disaccharide glycosides such as β-primeveroside (6-O-β-D-Xylopyranosyl-β-D-glucopyranoside) or the analogues thereof. In addition to these fragrances, some of colorants and physiologically active substances such as medicinal components are known to be present in the form of disaccharide glycoside or its analogue.

Enzymes having an action to cleave the disaccharide unit by acting on these fragrance components or disaccharide glycosides of physiologically active substance precursors have been isolated, for example, form tea leaves (see Patent Document 1). Although industrial application of these enzymes is attracting attention, the supply sources are limited, and thus, there was a strong need for development of a method of producing such an enzyme industrially and cost-effectively in a greater amount. On the other hand, it is also known that such a precursor disaccharide glycoside or the analogue is resistant to liberation of its aglycone with conventionally available β-glucosidases.

Under the circumstance above, the applicant had proposed a microorganism-derived diglycosidase that is readily produced from unlimited sources and has an enzyme activity to act on such a disaccharide glycoside, releasing its disaccharide sugar and aglycone (see Patent Document 2).

Patent Document 1: Japanese Unexamined Patent Publication No. 8-140675
Patent Document 2: WO 00/18931

However, the diglycosidase produced by *Aspergillus fumigatus* described in Patent Document 2 had a problem in safety, because *Aspergillus fumigatus* may possibly cause opportunistic infection. In addition, the enzyme was still unsatisfactory in enzyme activity and also in thermal stability, as it is inactivated at 55° C.

An object of the present invention is to provide a novel diglycosidase higher in safety, enzyme activity, and heat resistance than conventional diglycosidases, and a gene coding the same.

DISCLOSURE OF THE INVENTION

The inventors have found that it was possible to obtain a *Penicillium multicolor* TS-5 strain capable of producing a high-activity diglycosidase that was produced by mutation of high-safety *Penicillium multicolor* IAM7153 and that the diglycosidase produced by the strain was a new diglycosidase superior in heat resistance, compared to conventional diglycosidases and also different in molecular weight therefrom, and thus, accomplished the present invention.

The diglycosidase according to the present invention has an action to act on a disaccharide glycoside unavailable as a substrate by conventional β-glucosidases, releasing its disaccharide sugar and aglycone from the disaccharide glycoside. In the present description, the active enzyme will be referred to as a "diglycosidase".

The novel diglycosidase according to the present invention is an enzyme produced by a microorganism belonging to the genus *Penicillium*, having the following physicochemical properties:
(1) action and substrate specificity: it acts on a disaccharide glycoside, releasing the disaccharide sugar and the aglycone thereof;
(2) optimum pH: around 4.5;
(3) pH stability: it is stable at pH 4.0 to 8.0 under the processing condition at 37° C. for 30 minutes, and retains its 80% or more of the activity even after processing at pH 4.0 or lower;
(4) optimum temperature: around 60° C. in a sodium acetate-acetic acid buffer solution (pH 5.5);
(5) thermal stability: it is stable at 50° C. or lower in a sodium acetate-acetic acid buffer solution (pH 5.5) and retains 45% of the activity even after processing at 60° C. for 40 minutes;
(6) molecular weight: 40,000±5,000 Da based on SDS-PAGE measurement; and
(7) isoelectric point (pI): about 4.3.

In the present invention, the disaccharide glycoside may be β-primeveroside or a disaccharide glycoside similar to the same. The similar disaccharide glycoside is, for example, apiofuranosyl-β-D-glucopyranoside or arabinofuranosyl-β-D-glucopyranoside. In addition in these present inventions, the microorganism belonging to the genus *Penicillium* may be *Penicillium multicolor*. The *Penicillium multicolor* strain may be *Penicillium multicolor* TS-5 (FERM BP-10627).

Another aspect of the present invention is a protein (a), (b) or (c):
(a) a protein having the amino acid sequence represented by SEQ ID No. 6 in the sequence listing;
(b) a protein having the amino acid sequence represented by SEQ ID No. 6 in the sequence listing, one or more amino acids thereof being deleted, substituted or added thereto, having diglycosidase activity; or
(c) a protein having an amino acid sequence 65% or more homologous with the amino acid sequence represented by SEQ ID No. 6 in the sequence listing and having diglycosidase activity.

Yet another aspect of the present invention is a gene coding a following protein (a), (b) or (c):
(a) a protein having the amino acid sequence represented by SEQ ID No. 6 in the sequence listing;
(b) a protein having the amino acid sequence represented by SEQ ID No. 6 in the sequence listing, one or more amino acids thereof being deleted, substituted or added thereto, having diglycosidase activity; or
(c) a protein having an amino acid sequence 65% or more homologous with the amino acid sequence represented by SEQ ID No. 6 in the sequence listing and having diglycosidase activity.

Yet another aspect of the present invention is a gene containing a following DNA (a), (b) or (c):
(a) a DNA having the base sequence represented by SEQ ID No. 5 in the sequence listing;
(b) a DNA having the base sequence represented by SEQ ID No. 5 in the sequence listing, one or more bases thereof being deleted, substituted or added thereto, coding a protein having diglycosidase activity; or
(c) a DNA hybridizing with the DNA having the base sequence represented by SEQ ID No. 5 in the sequence listing under stringent condition and coding a protein having diglycosidase activity.

Yet another aspect of the present invention is a recombinant vector containing the gene. Yet another aspect of the present invention is a transformant, obtained by transforming a host cell with the recombinant vector.

Yet another aspect of the present invention is a method of producing a diglycosidase, characterized by including culturing the transformant in a medium, thus allowing production of the diglycosidase, and collecting the diglycosidase.

Yet another aspect of the present invention is a method of producing a diglycosidase, characterized by including culturing *Penicillium multicolor*, thus producing the diglycosidase having above-mentioned physicochemical properties, and collecting the diglycosidase. In the production method above, the *Penicillium multicolor* strain may be *Penicillium multicolor* TS-5 (FERM BP-10627).

The diglycosidase according to the present invention can be obtained with a microorganism belonging to the genus *Penicillium*, favorably *Penicillium multicolor*, more favorably *Penicillium multicolor* TS-5. *Penicillium multicolor* TS-5 is deposited to IPOD, as described below.

Name of depositary organization: International Patent Organism Depositary (IPOD) National Institute of Advanced Industrial Science and Technology (AIST)
    Address of depositary organization: ZIP: 305-8566, Tsukuba Central 6, 1-1-1 Higashi, Tsukuba, Ibaraki, Japan
Date of deposit: 29 Sep. 2004
Deposit number: FERM BP-10627

The microorganism submitted to the international depositary authority is the same as the original microorganism deposited on 29 Sep. 2004 (FERM P-20232).

The bacterial properties of *Penicillium multicolor* TS-5 are as follows:
1. Morphology (after Incubation on Czapek's Dox Agar Flat Plate or Malt Extract Agar at 25° C.)
(1) Conidiophore: length: 20 to 240 µm, diameter: 1.6 to 3.6 µm, smooth surface, bulging terminal, 3.2 to 5.2 µm
(2) Penicilli: single verticil
(3) Phialide: length 7.2 to 12 µm, diameter 2.4 to 3.2 µm
(4) Conidium: size: 2.4 to 3.2 µm, spherical to hypospherical, smooth surface, loose column-shaped chain formed
(5) Ascospore: not formed
(6) Sclerotium: not formed As described above, the strain, which has single-verticil penicilli, does not form ascospores, and grows slowly on Czapek agar, is grouped in the group of *Penicillium implicatum* to which *Penicillium multicolor, Penicillium implicatum*, and *Penicillium subkateritium* belong, according to Raper, K. B., Thom, C. & Fennell, D. I., A Manual of Penicillia. New York & London: Hafner Publishing Company (1968).

On the other hand, the strain, which has single-verticil penicilli, does not form ascospores, has smooth-surfaced spherical conidiums, and grows slowly, particularly in Sakaguchi & Wang agar medium, is identified as *Penicillium multicolor, Penicillium roseopurpureum,* or *Penicillium terlikowskii*, according to Abe, S., Studies on the classification of the Penicillia. J. Gen. Appl. Microbiol. 2, 1 to 344 (1956).

2. Chemical Taxonomic Properties

The inventors have conducted systematic analysis of the strain in the genealogical tree of the *Penicillium* species to which it belongs. The systematic analysis was performed in the following manner: First, it was found that the 28S rDNA D2 region of the present strain had the sequence represented by SEQ ID No. 18 in the sequence table (321 bases).

The inventors have compared, by using a homology search system BLAST, the base sequence of the 28S rDNA D2 region of the strain with that of the 28S rDNA D2 regions of each of known *Penicillium* strains (31 strains). However, four strains of *Penicillium multicolor* among known *Penicillium* strains did not have an accession number, and thus, the base sequence of each strain was determined in a similar manner to the 28S rDNA D2 region, showing that *Penicillium multicolor* NBRC 5725 and *Penicillium multicolor* NBRC 6042 were completely homologous with the present strain, while *Penicillium multicolor* NBRC 7569 and *Penicillium multicolor* NBRC 7817 were 98.3% homologous with the present strain. Table 1 shows the strains of Subgenus *Aspergilloides* used in the systematic analysis.

TABLE 1

| Species | Strain | Accession No. |
|---|---|---|
| Present Strain | | Sequence described above |
| Penicillium multicolor | NBRC 5725 | Completely homologous with the sequence above |
| Penicillium multicolor | NBRC 6042 | Completely homologous with the sequence above |
| Penicillium multicolor | NBRC 7569 | 98% homologous with the sequence above |
| Penicillium multicolor | NBRC 7817 | 98% homologous with the sequence above |
| Penicillium adametzii | NRRL 737 | AF033401 |
| Penicillium adametzioides | NRRL 3405 | AF033403 |
| Penicillium bilaiae | NRRL 3391 | AF033402 |
| Penicillium capsulatum | NRRL 2056 | AF033429 |
| Penicillium chermesinum | NRRL 735 | AF033413 |
| Penicillium citreonigrum | NRRL 761 | AF033456 |
| Penicillium cyaneum | NRRL 775 | AF033427 |
| Penicillium decumbens | NRRL 741 | AF033453 |
| Penicillium dimorphosporum | NRRL 5207 | AF081804 |
| Penicillium donkii | NRRL 5562 | AF033445 |
| Penicillium fellutanum | NRRL 746 | AF033399 |
| Penicillium fuscum | NRRL 721 | AF033443 |
| Penicillium glabrum | NRRL 766 | AF033407 |
| Penicillium implicatum | NRRL 2061 | AF033428 |
| Penicillium lividum | NRRL 754 | AF033406 |
| Penicillium purpurescens | NRRL 720 | AF033408 |
| Penicillium resedanum | NRRL 578 | AF033398 |
| Penicillium restrictum | NRRL 1748 | AF033457 |
| Penicillium roseopurpureum | NRRL 2064 | AF033415 |
| Penicillium sclerotiorum | NRRL 2074 | AF033404 |
| Penicillium spinulosum | NRRL 1750 | AF033410 |
| Penicillium thomii | NRRL 2077 | AF034448 |
| Penicillium turbatum | NRRL 757 | AF034454 |
| Penicillium velutinum | NRRL 2069 | AF033448 |
| Penicillium vinaceum | NRRL 739 | AF033461 |
| Penicillium waksmanii | NRRL 777 | AF033417 |
| Paecilomyces variotii | NRRL 1115 | AF033395 |

A genealogical tree including the present strain and other species in subgenus *Aspergilloides*, as determined based on the D2 region, is shown in FIG. 1. In the genealogical tree chart, Paecilomyces variotii is regarded as the outgroup. The scale bar is 0.01 Knuc.

The systematic analysis based on the base sequence of the 28S rDNA D2 region revealed that the strain, which formed a cluster with *Penicillium multicolor*, was a microorganism related to *Penicillium multicolor*. In addition, *Penicillium*

*multicolor* strains NBRC 5725 and NBRC 6042 were found to have the same sequence, and thus, the present strain is identified as a *Penicillium multicolor* strain and designated *Penicillium multicolor* TS-5.

The microorganisms belonging to the genus *Penicillium* can be cultured by a method or under a condition suitable for production of the diglycosidase according to the present invention, and the method and the condition are not particularly limited. For example, the microorganism may be grown in liquid culture or solid culture, preferably in liquid culture. The liquid culture is performed, for example, in the following manner: The medium for use is arbitrary, if it is suited for growth of the microorganism producing the diglycosidase according to the present invention.

It is, for example, a medium containing carbon sources such as glucose, sucrose, gentibiose, soluble starch, glycerol, dextrin, syrup, and organic acids; nitrogen sources such as ammonium sulfate, ammonium carbonate, ammonium phosphate, ammonium acetate, peptone, yeast extract, corn steep liquor, casein hydrolysate, wheat bran, and fillet extract; and inorganic salts such as potassium salt, magnesium salt, sodium salt, phosphate salt, manganese salt, iron salt, and zinc salt. In addition, various inducing agents for production and accumulation of the diglycosidase may be added to the medium. Examples of the inducing agents for use include saccharides, preferably gentose (e.g., Gentose #80, Nihon Shokuhin Kako Co., Ltd.), gentibiose, gentioligosaccharide (e.g., gentioligosaccharide, Wako Pure Chemical Industries, Ltd.), and the like. The addition amount of these inducing agents is not particularly limited, if it increases the production efficiency of the desirable diglycosidase, but preferably 0.01 to 5%. The pH of the medium is adjusted preferably, for example, to approximately 3 to 8, more preferably to approximately 5 to 6; the culture temperature is normally approximately 10 to 50° C., preferably approximately about 30° C.; and the culture is continued for 1 to 15 days, preferably 4 to 7 days, under aerobic condition. The culture method for use is, for example, shaking culture or aerobic submerged culture by using a jar fermenter. However, the culture condition and others described above are not particularly limited, if the condition is suitable for production of the diglycosidase according to the present invention.

The diglycosidase in the culture solution obtained is isolated and purified by a common method in combination of centrifugation, UF concentration, salting out, and various chromatographies for example by using ion-exchange resin. The culture solution of *Penicillium multicolor* may be used as it is as the diglycosidase according to the present invention. The purification degree of the culture solution can be adjusted properly according to the application of the present invention.

It is also possible to obtain the diglycosidase according to the present invention easily and efficiently, by separating the gene coding the diglycosidase and isolating the diglycosidase expressed therefrom.

Other embodiments of the diglycosidase according to the present invention include (a) a protein having the amino acid sequence represented by SEQ ID No. 6 in the sequence listing, (b) a protein having the amino acid sequence represented by SEQ ID No. 6 in the sequence listing, one or more of its amino acids thereof being deleted, substituted or inserted thereto, having diglycosidase activity, and (c) a protein having a sequence 65% or more homologous with the amino acid sequence represented by SEQ ID No. 6 in the sequence listing and having diglycosidase activity. Also included are proteins with the different degree of deletion, substitution or addition of amino acids in the range where the basic properties of the protein remain unchanged or are rather improved. These variants can be prepared by a known method. The homology is 65% or more, preferably 80% or more, and more preferably 90% or more.

The gene coding the diglycosidase according to the present invention can be extracted favorably from *Penicillium multicolor* TS-5. Alternatively, it may be prepared by chemical synthesis, for example, by the Fmoc method (fluorenylmethyloxycarbonyl method) or the tBoc method (t-butyloxycarbonyl method) or by a conventional method of using a peptide synthesizer available for example from Amersham Pharmacia Biotech. Yet alternatively, fragments containing the diglycosidase gene may be prepared by using polymerase chain reaction (hereinafter, PCR).

The genes coding the diglycosidase according to the present invention include (a) a gene coding the protein having the amino acid sequence represented by SEQ ID No. 6 in the sequence listing, (b) a gene coding protein having the amino acid sequence represented by SEQ ID No. 6 in the sequence listing, one or more of its amino acids thereof being deleted, substituted or added thereto, having diglycosidase activity, and (c) a gene coding the proteins having a sequence 65% or more homologous with the amino acid sequence represented by SEQ ID No. 6 in the sequence listing and having diglycosidase activity.

The genes coding the diglycosidase according to the present invention include (a) a DNA having the base sequence represented by SEQ ID No. 5 in the sequence listing, (b) a DNA having the base acid sequence represented by SEQ ID No. 5 in the sequence listing, one or more bases thereof being deleted, substituted or added thereto, coding a protein having diglycosidase activity, and (c) a DNA hybridizing with the DNA having the base sequence represented by SEQ ID No. 5 in the sequence listing under stringent condition and coding the protein having diglycosidase activity. Also included are DNAs with the different degree of deletion, substitution or addition of nucleotides in the range where the basic properties of the protein remain unchanged or are rather improved. Such variants may be prepared by a known method such as random or site-specific mutation. Examples of the methods of introducing random mutation include a chemical DNA-processing method of causing transition mutation by converting a cytosine base into a uracil base by action of sodium hydrogen sulfite [Proceeding of the National Academy of Sciences USA, 79, p. 1408 to 1412 (1982)] and a biochemical method of causing base substitution in the process of producing a double stranded chain in the presence of [α-S] dNTP [Gene, 64, p. 313 to 319 (1988)]. Examples of the methods of site-specific mutation include a method of using amber mutation [gapped duplex method, Nucleic Acids Research, 12, 24, p. 9441 to 9456 (1984)], methods of using the recognition site of restriction enzymes [Analytical Biochemistry, 200, p. 81 to 88 (1992) and Gene, 102, p. 67 to 70 (1991)], a method of using dUT (dUTase) and ung (uracil DNA glycosylase) mutation [Kunkel method, Proceeding of the National Academy of Sciences USA, 82, p. 488 to 492 (1985)], and the like. The "stringent condition" is, for example, hybridization at 6×SSC and 0.5% SDS at 68° C., or 6×SSC, 0.5% SDS and 50% formamide at 42° C.

The DNA coding the diglycosidase according to the present invention can be prepared for example, by cloning the gene from *Penicillium multicolor* TS-5 by the method described below. The diglycosidase according to the present invention is first isolated and purified by the method described above, and information on its partial amino acid sequence is obtained. The partial amino acid sequence may be determined, for example, by decomposing the purified enzyme directly by Edman degradation [Journal of Biological Chemistry, 256, p. 7990 to 7997 (1981)] according to a common method and supplying the product to an amino acid sequence analyzer [for example, Protein Sequencer 476A, manufactured by Applied Biosystems], or by performing restricted hydrolysis thereof by action of a proteinase, separating and purifying the peptide fragments obtained, and analyzing the amino acid sequence of the purified peptide fragments obtained. The DNA coding the diglycosidase according to the present invention is cloned, based on the information on the partial amino acid sequence thus obtained. Generally, the cloning is performed, for example, by a method of using PCR or hybridization.

The hybridization method, when used, is performed by a method described, for example, in Molecular Cloning, A Laboratory Manual, T. Maniatis et al., Cold Spring Harbor Laboratory, 1989.

Alternatively, the PCR method, when used, is performed in the following manner: First, a desired gene fragment is obtained by using the genome DNA of a microorganism producing the diglycosidase according to the present invention as the template and conducting PCR reaction while using a synthetic oligonucleotide primer designed based on the information on the partial amino acid sequence. The PCR method is carried out according to the method described, for example, in PCR Technology [Erlich H. A. Ed., Stockton Press, published in 1989]. When the base sequence of the DNA fragment amplified by a commonly-used method, for example by the dideoxy chain terminator method, is determined, the sequence corresponding to the partial amino acid sequence of the enzyme according to the present invention is found in the determined sequence, in addition to the sequence of the synthetic oligonucleotide primer, to give part of the desired enzyme gene according to the present invention. It is possible to clone a gene coding the entire length of the diglycosidase according to the present invention, for example, by continuing hybridization method by using the obtained gene fragment as a probe. It is also possible to obtain a desired gene by chemical synthesis, based on the information on the base sequence [reference literature: Gene, 60 (1), p. 115 to 127 (1987)].

It is possible to produce the protein having the enzyme activity according to the present invention by transforming a host with the recombinant vector containing the gene coding the diglycosidase according to the present invention and then culturing the transformant under a condition commonly used. It is also possible to produce the diglycosidase according to the present invention in various hosts, by connecting a suitable combination of heterologous or homologous promoters and signal sequences to upstream of the mature DNA coding the diglycosidase. The host for use is, for example, a microorganism, an animal cell, a plant cell, or the like. Examples of the microorganisms include bacteria such as *E. coli, bacillus, Streptomyces*, and *lactococcus*; yeasts such as *saccharomyces, pichia*, and *kluyveromyces*; fungi such as *aspergillus, penicillium, trichoderma*, and *rhizopus*; and the like. Examples of the animal cells include baculovirus strains.

It is simple and easy to confirm expression and the products expressed, by using an antibody to the enzyme according to the present invention, but the expression may be evaluated by measuring the activity of the enzyme according to the present invention.

As described above, the enzyme according to the present invention may be purified from the transformant culture, for example, in proper combination of various methods such as centrifugation, UF concentration, salting out, ion-exchange resin and chromatography.

Hereinafter, various applications of the diglycosidase according to the present invention will be described. The diglycosidase can be used for strengthening the fragrance, color, and physiologically activity of various components such as vegetable materials and also for adjustment of the extraction efficiency of these components. Accordingly, it may be used in production of foods and beverages higher in fragrance, spices and flavoring agents higher in fragrance, perfume and others, and also in preliminary removal of unfavorable odor during processing for the production described above. As for color, it may be used for acceleration of color development and improvement in the color tone of vegetable materials, foods, and beverages and also for production of colorants. In addition, similarly to the fragrance components above, it may also be used for decomposition and removal of colorant precursors undesirable for quality, and as for physiologically active, it may be used for improvement of the action of medicinal components in crude drugs, herbs, others plant-derived components and physiologically active components and for decomposition of undesirable components. It is thus possible to obtain the action described above, by making the diglycosidase according to the present invention act on various disaccharide glycoside components. It is also possible to make physiologically active substances and others absorbed in the body more efficiently, by administering the diglycosidase according to the present invention together with a physiologically active substance or the like at the same time as blended or at a short interval separately without blending.

The preparation containing the disaccharide glycoside according to the present invention is not particularly limited, if it is hydrolyzed by the diglycosidase, and it is used for production of foods, cosmetics, medicines, quasi drugs, agricultural chemicals, feedstuffs and others, and more specifically for production of various toiletry products, fragrant foods, woodwork products, industrial plant-derived products such as straw tatami mat.

The products to which the diglycosidase according to the present invention is favorably applied include foods containing a fragrance component. More specifically, it may be used for example in the "withering" step in production of Oolong tea or jasmine tea, and also for improvement in fragrance of black tea (for example, tea-bag black tea by CTC method) and wine. Further, it may be used for preservation of fragrance of cosmetics, perfumes, and medicines and for improvement of pharmaceutical action.

It is also useful in production of colorants. It is possible to extract colorants more efficiently than before, for example in extraction of ruberythric acid-based alizarin dye from madder.

It is also possible to produce a precursor (disaccharide glycoside), by reacting a fragrance, colorant or physiologically active ingredient with a disaccharide component such as primeverose with the diglycosidase. Glycosidization of these components would be effective for improvement in the stability and storage life and detoxification of the component and for establishment of a drug delivery system of the medicinal component.

In addition, the diglycosidase decomposes modified glucosides such as acetyl glucoside, malonyl glucoside, methyl glucoside, phosphoglucoside, and amide glucoside, which are unavailable as substrate by conventional $\beta$-glucosidases, more efficiently than conventional $\beta$-glucosidases. It is possible to improve the absorption efficiency and the yield of isoflavones, by converting the isoflavone acetylglucosides and malonylglucosides contained in soybean into the aglycone form.

It is also possible to strengthen the fragrance of cut flower, for example by spraying a solution of the enzyme or making it adsorbed therein.

The methods of using the diglycosidase, specifically its addition method, addition amount, reaction method, and others, may be altered as needed. In a typical use method, the diglycosidase according to the present invention is added to a plant extract or a fermentation product containing fragrance precursors, and the mixture is incubated. The condition is not particularly limited, if the diglycosidase according to the present invention releases a fragrance, colorant, or physiologically active ingredient in reaction with the precursor for the fragrance, colorant, o physiologically active ingredient, and such as optimal condition can be determined easily without difficulty by those who are skilled in the art. It is possible to increase the concentration of the particular component under the condition above.

It is also possible to use the enzyme according to the present invention, for increase in the concentration of the fragrance, colorant, and physiologically active ingredient present in plants. Because plants contain precursors for these components, it is possible to raise the concentration of the fragrance, colorant, and physiologically active ingredient in plants, by adding an effective amount the diglycosidase according to the present invention to the plant (for example by genetic engineering) and cultivating the plant under the condition allowing hydrolysis of the precursors in the plant. It is also possible to adjust the timing of the plant generating the fragrance, colorant or physiologically active ingredient, by using the enzyme composition according to the present invention.

DESCRIPTION OF THE PREFERRED EMBODIMENTS

Hereinafter, the present invention will be described with reference to Examples, but it should be understood that the present invention is not restricted by the following Examples. In the description below, % represents w/v %, unless specified otherwise. The β-primeverosidase described below is an enzyme included in a class of diglycosidases that has an action similar to that of diglycosidase, and thus, these two enzymes may be used below without distinction.

Comparative Example

Method of Measuring Enzyme Activity

1. Method of Measuring β-Primeverosidase Activity

27 μl of a sample solution containing a particular amount of composition is mixed with 120 μl of a solution of para-nitrophenyl(pNP)-β-primeveroside dissolved in 20 mM citrate buffer solution (pH 4.7) to a concentration of 2 mM; the mixture is allowed to react at 37° C. for 302 seconds; 150 μl of 0.5 M aqueous sodium carbonate solution is added thereto; the absorbance of the resulting solution at 405 nm after 276 seconds is determined in an automatic biochemical analyzer (manufactured by Shimadzu Corporation, CL-8000). The absorbance of the sample-derived blank solution is determined similarly, as the substrate solution is replaced with 20 mM citrate buffer solution (pH 4.7). With a relationship between the absorbance at 405 nm and the concentration of para-nitrophenol, it is possible to convert the measured value in the automatic biochemical analyzer to the amount of the free para-nitrophenol generated in the enzyme reaction.

A unit of the enzyme is defined as an enzyme amount liberating 1 μmole of para-nitrophenol in a reaction period of 1 minute under the condition above.

The pNP-β-primeveroside was prepared by binding one xylose residue to pNP-β-glucoside via β-1,6 bond, in reaction of pNP-β-glucoside (manufactured by Merck & Co., Inc.) and xylooligosaccharide (manufactured by Wako Pure Chemical Industries) in the presence of an enzyme β-xylosidase (manufactured by sigma).

2. Method of Measuring β-Glucosidase Activity

27 μl of a sample solution containing a particular amount of composition is mixed with 120 μl of a solution of para-nitrophenyl(pNP)-β-glucoside dissolved in 20 mM citrate buffer solution (pH 4.7) to a concentration of 2 mM; the mixture is allowed to react at 37° C. for 302 seconds; 150 μl of 0.5 M aqueous sodium carbonate solution is added thereto; the absorbance of the resulting solution at 405 nm after 276 seconds is determined in an automatic biochemical analyzer (manufactured by Shimadzu Corporation, CL-8000). The absorbance of the sample-derived blank solution is determined similarly, as the substrate solution is replaced with 20 mM citrate buffer solution (pH 4.7). With the relationship between the absorbance at 405 nm and the concentration of para-nitrophenol, it is possible to convert the measured value in the automatic biochemical analyzer to the amount of the free para-nitrophenol generated in the enzyme reaction.

A unit of the enzyme is defined as is an enzyme amount liberating 1 μmole of para-nitrophenol in a reaction period of 1 minute under the condition.

3. Method of Measuring β-Xylosidase Activity

27 μl of a sample solution containing a particular amount of composition is mixed with 120 μl of a solution of para-nitrophenyl (pNP)-β-xyloside dissolved in 20 mM citrate buffer solution (pH 4.7) to a concentration of 2 mM; the mixture is allowed to react at 37° C. for 302 seconds; 150 μl of 0.5 M aqueous sodium carbonate solution is added thereto; the absorbance of the resulting solution at 405 nm after 276 seconds is determined in an automatic biochemical analyzer (manufactured by Shimadzu Corporation, CL-8000). The absorbance of the sample-derived blank solution is determined similarly, as the substrate solution is replaced with 20 mM citrate buffer solution (pH 4.7). With the relationship between the absorbance at 405 nm and the concentration of para-nitrophenol, it is possible to convert the measured value in the automatic biochemical analyzer to the amount of the free para-nitrophenol generated in the enzyme reaction.

A unit of the enzyme is defined as is an enzyme amount liberating 1 μmole of para-nitrophenol in a reaction period of 1 minute under the condition.

4. Method of Measuring Quasi-β-Primeverosidase Activity

Primeverose is a disaccharide consisting of xylose and glucose. β-Xylosidase and β-glucosidase in combination show a quasi-β-primeverosidase activity (apparent β-primeverosidase activity). For evaluation of the influence of the quasi-β-primeverosidase activity by these foreign enzymes on the β-primeverosidase activity above, a fraction containing β-xylosidase and β-glucosidase but not containing β-primeverosidase was prepared, by fractionation of the culture broth of *Penicillium multicolor* IAM7153; and the method of calculating the quasi-β-primeverosidase activity was determined by comparison of the activities of the both enzymes with the activity of β-primeverosidase.

As a result, when the ratio of [β-xylosidase activity]:[β-glucosidase activity] is 1:1, $1/10$ of the β-primeverosidase activity is found to represent the quasi-β-primeverosidase activity, and thus, the $1/10$ value was defined as the quasi-β-primeverosidase activity.

Example 1

Culture of *Penicillium multicolor* IAM7153

*Penicillium multicolor* IAM7153 was grown, for more efficient production of the diglycosidase. The *Penicillium multicolor* IAM7153 is obtained as a type culture from the Institute of Molecular and Cellular Biosciences, the University of Tokyo.

*Penicillium multicolor* IAM7153 was inoculated on a slant potato dextrose agar medium (potato extract: 200 g/L, glucose: 20 g/L, agar: 15 g/L, pH: 5.6±0.2) and incubated at 27 to 30° C. for 10 to 14 days. 10 ml of sterilized 0.9% Tween 80 solution was added to the slant face on which the microorganism has grown sufficiently, allowing suspension of the conidia. The conidium suspension was filtered through a sterilized glass filter G3 (manufactured by Hario), to give a conidium solution. The conidia obtained was washed and resuspended in 10 mL of 0.9% Tween 80 solution.

The conidium suspension of *Penicillium multicolor* IAM7153 was irradiated with ultraviolet ray (15-W UV lamp, distance: 50 cm). After UV irradiation under a condition at a fatality rate of 99.99%, the spore suspension was diluted properly and applied on a flat-plate dextrose agar medium. The colony appearing thereon after incubation at 30° C. for 7 to 10 days was streaked on a slant potato dextrose agar medium (potato extract: 200 g/L, glucose: 20 g/L, agar: 15 g/L, pH: 5.6±0.2), and the medium was incubated at 27 to 30° C. for 10 to 14 days, until favorable spores are formed. The microorganism in the area of approximately 5 mm square on the slant medium after sufficient growth was separated with a sterilized platinum loop and inoculated into a preculture medium.

The following nutrient solution was used as the preculture medium: Preculture medium: defatted soybean (Honen): 20 g/L, glucose: 30 g/L, $KH_2PO_4$: 5 g/L, $(NH_4)_2SO_4$: 4 g/L, dry yeast (Kirin Brewery Company): 3 g/L, Adecanol LG-126 (Asahi Denka): 0.5 mL/L, pH not adjusted. 100 mL of the medium was placed in a 500-mL Shaking flask and sterilized at 121° C. for 20 minutes. After inoculation of the microorganism, the medium was incubated at 27±1° C. and a shaking velocity of 140 rpm for 5 days.

The following nutrient solution was used as the production medium. Production medium: Sunfiber R (Taiyo Kagaku Co., Ltd.): 10 g/L, $KH_2PO_4$: 20 g/L, $(NH_4)_2SO_4$: 10 g/L, Meast PIG (Asahi Breweries, Ltd.): 31.3 g/L, Adecanol LG-126 (Asahi Denka): 0.5 mL/L, pH not adjusted. 100 mL of the medium was placed in a 500-mL Shaking flask and sterilized at 121° C. for 20 minutes. 1 mL of the solution after preculture was inoculated, and the medium was incubated at 27±1° C. and a shaking velocity of 140 rpm for 10 days.

The enzyme-producing capability of the strain was determined by analyzing the diglycosidase activity of the culture solution obtained. The strains giving a culture solution higher in the diglycosidase activity were selected as favorable strains. The strains were further subjected to mutation, and the operation of selecting favorable strains was repeated four times, to give *Penicillium multicolor* TS-5, which is approximately 100 times higher in diglycosidase productivity than *Penicillium multicolor* IAM7153.

Example 2

Purification of the Diglycosidase Produced by *Penicillium multicolor* TS-5

*Penicillium multicolor* TS-5 was streaked on a slant potato dextrose agar medium (potato extract: 200 g/L, glucose: 20 g/L, agar: 15 g/L, pH: 5.6±0.2), and the medium was incubated at 27 to 30° C. for 10 to 14 days, until favorable spores were formed. The microorganism in an area of approximately 5 mm square on the sufficiently grown slant medium was separated with a sterilized platinum loop and inoculated into a preculture medium.

The following nutrient solution was used as the preculture medium: Preculture medium: defatted soybean (Honen): 20 g/L, glucose: 30 g/L, $KH_2PO_4$: 5 g/L, $(NH_4)_2SO_4$: 4 g/L, dry yeast (Kirin Brewery Company): 3 g/L, Adecanol LG-126 (Asahi Denka): 0.5 mL/L, pH not adjusted. 100 mL of the medium was placed in a 500-mL Shaking flask and sterilized at 121° C. for 20 minutes. After inoculation of the microorganism, the medium was incubated at 27±1° C. and a shaking velocity of 140 rpm for 5 days.

The following nutrient solution was used as the production medium. Production medium: Sunfiber R (Taiyo Kagaku Co., Ltd.): 10 g/L, $KH_2PO_4$: 20 g/L, $(NH_4)_2SO_4$: 10 g/L, Meast PIG (Asahi Breweries, Ltd.): 31.3 g/L, Adecanol LG-126 (Asahi Denka): 0.5 mL/L, pH not adjusted. 100 mL of the medium was placed in a 500-mL Shaking flask and sterilized at 121° C. for 20 minutes. 1 mL of the solution after preculture was inoculated, and the medium was incubated at 27±1° C. and a shaking velocity of 140 rpm for 10 days. 900 ml of the culture solution thus obtained was filtered through a TOYO filter paper No. 2, and the filtrate was centrifuged at 17,000 G for 20 minutes (Kubota 7700, rotor: KAKB-10.500), to give 750 ml of an enzyme-containing solution as the centrifugal supernatant.

The enzyme-containing solution was fractioned at ammonium sulfate-saturation concentrations of 60% to 80%; the resulting precipitate was dissolved in 20 mM acetate buffer solution at pH 4.7 and separated into a β-glucosidase fraction and a β-xylosidase-active fraction by column chromatography by using a Phenyl Sepharose resin. The diglycosidase fraction obtained by the Phenyl Sepharose column chromatography was demineralized and concentrated with an ultrafiltration membrane and then, adsorbed and eluted by isoelectric chromatography (Mono-PHR5/20 (Pharmacia)), to give a diglycosidase fraction. Analysis by SDS-PAGE of the diglycosidase fraction obtained gave a single band, showing that the diglycosidase was purified sufficiently.

Hereinafter, physical and chemical properties the diglycosidase obtained will be described.

The optimum pH was determined in the following manner: 90 μl of the enzyme solution containing the pure diglycosidase obtained above was added to 400 μl of 2 mM pNP-β-primeveroside solution adjusted to particular pH with 20 mM sodium acetate-HCl buffer solution at pH 2.0 to 4.0, 20 mM sodium acetate buffer solution at pH 4.0 to 5.5, or 20 mM $Na_2HPO_4$—$KH_2PO_4$ buffer solution at pH 5.5 to 8.0, and the mixture was allowed to react at 37° C. for 10 minutes. 500 μl of 0.5 M sodium carbonate solution was added thereto for termination of the reaction, and the activity thereof was determined by measuring the absorbance at 420 nm. As a result, the optimum pH was found to be around 4.5 (see FIG. 2).

The pH stability was determined in the following manner: The enzyme solution containing the purified diglycosidase was diluted 100 times with 20 mM sodium acetate-HCl buffer solution at pH 2.0 to 4.0, 20 mM sodium acetate buffer solution at pH 4.0 to 5.5, or mM $Na_2HPO_4$—$KH_2PO_4$ buffer solution at pH 5.5 to 8.0; the solution at each pH was processed at 37° C. for 30 minutes, and 90 μl thereof was then mixed with 400 μl of 2 mM pNP-β-primeveroside solution (pH 4.5) preheated at 37° C. for 5 minutes; and the mixture was allowed to react for 10 minutes. 500 μl of 0.5 M sodium carbonate solution was added thereto for termination of the reaction; and the activity thereof was determined by measuring the absorbance at 420 nm. As a result, the enzyme was stable in a pH range of 4.0 to 8.0 (see FIG. 3).

The optimum temperature was determined in the following manner: 90 μl of the enzyme solution of purified diglycosidase was added to 400 μl of 2 mM pNP-β-primeveroside solution prepared with 20 mM sodium acetate-acetic acid buffer (pH 5.5), and the mixture was allowed to react at 20 to 80° C. for 10 minutes. 500 μl of 0.5 M sodium carbonate solution was added thereto for termination of the reaction, and the activity thereof was determined by measuring the absorbance at 420 nm. As a result, the optimum temperature was found to be around 60° C. (see FIG. 4).

The thermal stability was determined in the following manner: The enzyme solution of purified diglycosidase dissolved in 20 mM sodium acetate-acetic acid buffer (pH 5.5) was processed at temperatures of 20 to 80° C. for 30 minutes, and the thermal stability was evaluated by measuring the remaining activity. As a result, the enzyme retained its 90% or more of its original activity at a temperature of 50° C. or lower and 60% of the activity after treatment at 60° C. (see FIG. 5).

Alternatively, the molecular weight of the purified diglycosidase, as determined by SDS-PAGE, was 40000±5000 daltons (see FIG. 6), and the isoelectric point pI was approximately 4.3.

In Table 2, physical and chemical properties of the diglycosidase produced by the *Penicillium multicolor* TS-5 (inventive enzyme) are compared with those of the tea-derived diglycosidase (tea-derived enzyme) described in Patent Document 1 and the *Aspergillus fumigatus*-derived diglycosidase (Asp. fumigatus-derived enzyme) described in Patent Document 2. The inventors also compared the thermal stability of the inventive enzyme with that of the Asp. fumigatus-derived enzyme under the same condition. Specifically, each enzyme was treated with 20 mM sodium acetate-acetic acid buffer (pH 5.5) at 60° C. for 10 to 60 minutes, and the residual activity was determined. As a result, the inventive enzyme retained 45% of its original activity even after treatment at 60° C. for 40 minutes, while the Asp. fumigatus-derived enzyme lost its entire activity after treatment at 60° C. for 40 minutes (see FIG. 7).

TABLE 2

|  | Inventive enzyme | Tea-derived enzyme | *Asp. fumigatus*-derived enzyme |
|---|---|---|---|
| Optimum pH | Around 4.5 | 4.0 to 6.0 | 2.5 to 3.0 |
| Optimum temperature | Around 60° C. | Arond 50° C. | — |
| pH stability | 4.0 to 8.0 | 4.0 to 7.0 | 3.0 to 8.0 |
| Thermal stability | Stable at 50° C. or lower (pH 5.5), retains 45% of its activity after treatment at 60° C. for 40 minutes (pH 5.5) | Stable at 45° C. or lower (pH 8.0) | Stable at 50° C. or lower (pH 8.0), completely inactivated after treatment at 60° C. for 40 minutes (pH 5.5) |
| Molecular weight (dalton) | 40,000 ± 5,000 | 61,000 | 47,000 |

As obvious from Table 2, the diglycosidase produced by the *Penicillium multicolor* TS-5 strain was far superior in thermal stability to conventional diglycosidases and the molecular weight thereof was also different. Therefore, the diglycosidase produced by the *Penicillium multicolor* TS-5 was found to be a novel diglycosidase.

Example 3

Isolation and Analysis of Diglycosidase Gene

1. Determination of the N-Terminal Amino Acid Sequence of Diglycosidase

The amino acid sequence of the diglycosidase produced by the *Penicillium multicolor* TS-5 was analyzed.

The diglycosidase obtained in Example 2 was analyzed in a protein sequencer (manufactured by Hewlett-Packard Development Company), to give the N-terminal 15-residue amino acid sequence shown by SEQ ID No. 1:

SEQ ID No. 1:
Ser-Thr-Tyr-Leu-Asn-Trp-Thr-Thr-Phe-Asn-Ala-Val-

Gly-Ala-Asn

2. Extraction of Chromosomal DNA

*Penicillium multicolor* TS-5 was subjected to shaking culture in a YPD medium for 3 days; the microorganism obtained was collected by filtration through a No. 2 filter paper (Advantech) in a Buechner funnel and washed with sterile water. After removal of excess water, the microorganism was frozen at −80° C. and freeze-dried in FREEZONE (LABCONCO). After drying, the solid mass was pulverized into a fine powder with sea sand in a mortar, and 12 ml of extraction solution [3.3% SDS, 10 mM Tris-HCl (pH 7.5), 1 mM EDTA] was added to the pulverized microorganism and the mixture was agitated. The lysate thus obtained was extracted with phenol/chloroform for removal of foreign proteins; isopropanol in the same amount was added thereto; and the isolated DNA was collected with a glass rod. The DNA was dissolved in a TE solution containing 0.1 mg/ml RNase; the mixture was allowed to react at 37° C. for 30 minutes; a TE solution containing 0.2 mg/ml proteinase K was added additionally; and the mixture was allowed to react at 37° C. for 30 minutes. The solution was extracted with phenol/chloroform, and the latter was precipitated with 2.5-volume of cold ethanol. The precipitate was immersed in 70% ethanol and then, dried, and redissolved in the TE solution.

3. Preparation of Messenger RNA

*Penicillium multicolor* TS-5 was subjected to shaking culture at 27° C. for 4 days in a medium in the composition of Amalty sirup: 3%, soybean cake: 1%, Bacto peptone (or polypeptone) 4%, and $KH_2PO_4$ 2% [pH 5.5]; and the microorganism obtained was collected by filtration through a No. 2 filter paper (Advantech) in a Buechner funnel and washed with sterile water. After removal of excess water, the microorganism was pulverized with a pestle in a mortar while frozen in liquid nitrogen. One ml of Trizole reagent (manufactured by Invitrogen) was added to the pulverized microorganism, and the suspension was transferred into a tube. After the mixture was left still for 5 minutes, it was added with 0.2 ml of chloroform, and the mixture was thoroughly agitated and then left still at room temperature for 3 minutes. The suspension was centrifuged into upper and lower layers, and the upper layer was transferred into another tube. Subsequently, 0.5 ml of isopropanol was added, and the mixture was left still at room temperature for 10 minutes. Centrifugation and removal of the supernatant gave gel-like sediment. After addition of 1 ml of 75% ethanol, the mixture was centrifuged. The precipitate was redissolved in RNase-free water, to give a total RNA solution. mRNA was purified from the total RNA by using Micro Fast Track Kit 2.0 (manufactured by Invitrogen). The purification was performed according to the operation manual attached to the kit.

4. Preparation of Diglycosidase Gene-Specific DNA Fragment (3'-RACE)

Three kinds of mix primers shown below were designed, based on the 15-amino acid sequence information obtained by analysis of the N-terminal amino acid sequence of the diglycosidase produced by the *Penicillium multicolor* TS-5. N was replaced with I (inosine) during synthesis.

```
LD-A:    5'ACNTAYYTNAAYTGGAC3'      SEQ ID No. 2
LD-B:    5'TGGACNACNTTYAAYGC3'      SEQ ID No. 3
LD-C:    5'TTYAAYGCNGTNGGNGC3'      SEQ ID No. 4
```

3'-RACE (3'-Rapid Amplification of cDNA Ends) reaction was carried out by using the mRNA of *Penicillium multicolor* TS-5 as the template and also using the primer above. The 3'-RACE reaction was carried out by using 3'-Full RACE Core Set (manufactured by Takara Bio Inc.), according to the method in the attached manual. A DNA fragment of approximately 1,400 bp was prepared by amplification with any primer.

The base sequence of the LD-A primer-amplified fragment (DG1400A) was determined by using the LD-B primer, and a base sequence of approximately 800 bp was determined. Examination of the amino acid sequence based on the base sequence information obtained indicated presence of an open reading frame. The LD-B primer-amplified PCR fragment was subcloned into pBluescriptII KS(+).

5. Construction of Gene Library and Screening of Diglycosidase Gene

The chromosomal DNA produced from *Penicillium multicolor* TS-5 was digested with a restriction enzyme in combination with BglII. Southern blotting analysis was performed by using each restriction enzyme-processed solution obtained. In the analysis, a 1.4 Kb PCR fragment DNA amplified with the LD-B primer was used as the probe. A restriction enzyme map constructed from the results confirmed that EcoRI-SpeI digestion gave a single band of approximately 6,000 base pairs.

After complete digestion of the chromosomal DNA with EcoRI-SpeI, a DNA fragment having a length of approximately 6,000 base pairs was collected and purified by agarose gel electrophoresis. The DNA was inserted into the multi-cloning site of vector pUC19; *E. coli* was transformed with the vector; and a gene library was constructed.

Screening by colony hybridization was performed with the gene library thus prepared, by using the PCR fragment of approximately 1.4 Kb amplified with the LD-B primer as the probe. Probe labeling and signal detection during the colony hybridization were performed by using a DIG nucleic acid detection kit (manufactured by Roche). The operation was performed according to the method described in the operation manual attached.

After screening, two positive clones were obtained. A plasmid (pBNDG) was prepared from each clone, and the sizes of the inserted DNA fragment and the diglycosidase gene region were determined, by analysis of each plasmid. The base sequence of the region possibly containing the diglycosidase gene was determined, and the base sequence of the diglycosidase gene was identified to be that of SEQ ID No. 5 in the sequence listing. The amino acid sequence of the mature protein was estimated from the amino acid sequence estimated from the base sequence and N-terminal amino acid sequence of the diglycosidase. The estimated molecular weight of the mature protein was 39,997 daltons, and the estimated isoelectric point (pI) was 4.52. The amino acid sequence of the mature diglycosidase estimated from the gene sequence is shown as the SEQ ID No. 6 in the sequence listing. As shown by the sequence of SEQ ID No. 7 in the sequence listing, which corresponds to the open reading frame of the gene, the entire precursor protein has 389 amino acids, and N-terminal 23 residues are considered to be the pre-region, and the other 366 residues correspond to the mature protein. The protein according to the present invention and the gene containing a DNA coding the same include amino acid sequences and base sequences longer than the amino acid sequence shown by SEQ ID No. 6 and the base sequence shown by SEQ ID No. 5 (e.g., precursor protein and gene).

Example 4

Establishment of *Penicillium multicolor*-Transforming System

A. Isolation of Orotidine-5'-Phosphate Decarboxylase-Deficient Strain

After UV irradiation of the suspension of *Penicillium multicolor* IAM7153 conidia, the spores were coated on a 5-fluoroorotic acid (5-FOA) medium (Boeke et al., Mol. Gen. Genet. 197: 345-346, 1984) and incubated at 27° C. for 6 to 8 days. The 5-FOA-resistant strain grown was picked up respectively onto a minimal medium (0.3% $NaNO_3$: 0.05% KCl, 0.05% $MgSO_4.7H_2O$, 0.001% $FeSO_4.7H_2O$, 0.1% $KH_2PO_4$, 2% glucose, 1.5% agar, pH 6.0) and a minimal medium containing 5 mM uracil respectively, and the media were incubated at 27° C. for 3 to 5 days. The uracil-demanding strain growing only on the minimal medium containing 5 mM uracil was inoculated into a YPM medium containing 5 mM uridine (1% yeast extract, 2% peptone, 2% maltose, pH 6.0) and incubated at 27° C. and 140 rpm for 3 days by shaking culture. 1 g of the hypha and 1 g of sea sand were placed in a mortar cooled on ice and were pulverized sufficiently therein, and 10 ml of 50 mM Tris-HCl (pH 8.0) was added to the mortar, to give a suspension of the hypha. The suspension was centrifuged at 36,000×g for 10 minutes, for separation of the supernatant. The orotic acid phosphoribosyltransferase (OPRTase) activity of the supernatant was determined according to the method of Belser et al., (Meth. Enzymol. 51: 155-167, 1978), and the active strain was regarded as an orotidine-5'-phosphate decarboxylase-deficient strain (IAM7153ΔpyrG) (Horiuchi et al., Curr. Genet. 27: 472-478, 1995).

B. Cloning of the Marker Gene, Orotidine-5'-Phosphate Decarboxylase Gene

1. Preparation of pyrG-Specific PCR Fragment

Based on regions higher in homology of known orotidine-5'-phosphate decarboxylase genes: *Penicillium chrysogenum* pyrG (Cantoral et al., Nucleic Acid Res. 16 (16): 8177, 1988), *Aspergillus oryzae* pyrG (EMBL Acc. No. Y13811), *Aspergillus niger* pyrG (Wilson et al., Nucleic Acid Res. 16 (5): 2339, 1988), *Aspergillus nidulans* pyrG (Oakley et al., Gene 61: 385-399, 1988), and *Aspergillus fumigatus* pyrG (Weidner, Curr. Genet. 33 (5): 378-385, 1988), the following six kinds of mixed oligonucleotides were prepared in a DNA synthesizer and used as PCR primers,

```
Sense primer:
                                        SEQ ID No. 8
5'-GCGCCCTGCAGGATGTC(CGT)TC(CG)AAGTC(CG)CA(AC)
(CT)T-3'
```

-continued

Sense primer:
SEQ ID No. 9
5'-GCGCCCTGCAGGCACATCGA(CT)ATCCTC(AT)C(CT)GA-3'

Sense primer:
SEQ ID No. 10
5'-GCGCCCTGCAGGAAGCACAA(CT)TT(CT)(CT)T(CGT)ATCT T-3'

Sense primer:
SEQ ID No. 11
5'-GCGCCCTGCAGGGA(AG)GA(CT)CGCAA(AG)TTCATCGA-3'

Antisense primer:
SEQ ID No. 12
5'-GCGCCCTGCAGGTG(AG)TA(CT)TGCTG(ACT)CC(ACG)AGCT T-3'

Antisense primer:
SEQ ID No. 13
5'-GCGCCCTGCAGGAT(AG)AT(AG)AAGTC(ACGT)GCACC(TCG) CG-3'

PCR reactions were performed in a GeneAmp PCR System 9600 (Perkin Elmer) by using these primers and the chromosomal DNA of *Penicillium multicolor* IAM7153, which was prepared in a similar manner to the chromosomal DNA of *Penicillium multicolor* TS-5 described above, as templates, under the following condition;
<PCR Reaction Solution>
10×PCR reaction buffer solution (Perkin Elmer) 10 µl
dNTP mixture solution (each 2 mM, Perkin Elmer) 10 µl
25 mM $MgCl_2$ (Perkin Elmer) 6 µl
Chromosomal DNA solution (100 µm g/ml) 1 µl
50 µM Sense primer 2 µl
50 µM Antisense primer 2 µl
Sterile water 68.5 µl
Amplitaq Gold (5u/µl, Perkin Elmer) 0.5 µl
<PCR Reaction Condition>
Stage 1: Denaturation (95° C., 9 minute) 1 cycle
Stage 2: Denaturation (94° C., 45 second) 30 cycles
Annealing (55° C., 1 minute)
Extension (72° C., 2 minute)
Stage 3: Extension (72° C., 10 minute) 1 cycle The reaction solution was analyzed by electrophoresis with 0.6% TAE-agarose gel. PCR fragments were identified in combinations of SEQ ID Nos. 8 and 12, 8 and 13, 9 and 12, 9 and 13, 10 and 12, 10 and 13, 11 and 12, and 11 and 13. The base sequences of respective PCR fragments were identical with each other, except the primer sequence. Each PCR fragment was digested by a restriction enzyme Sse8387I, and then, the digested fragment was recovered by agarose electrophoresis and cloned into the Sse8387I site of puc19 (TOYOBO).

2. Construction of Genome Library and Screening

A genome DNA library was constructed by transforming a competent cell DH5 (TOYOBO), with a plasmid DNA obtained by digesting the chromosomal DNA of *Penicillium multicolor* IAM7153 with a restriction enzyme SmaI, recovering the digested fragment by agarose electrophoresis, and connecting the fragment to the SmaI site of pUC19 (TOYOBO).

The cloned PCR fragment obtained above in 1 was labelled with DIG-High Prime (manufactured by Roche), and screening was performed by using the labelled fragment as a DNA probe. After hybridization at 42° C. overnight by using DIG Easy Hyb Granules (manufactured by Roche), the filter was washed with 2×SSC/0.1% SDS (room temperature) and 0.5× SSC/0.1% SDS (68° C.). Subsequent analysis with DIG Nucleic Acid Detection Kit (manufactured by Roche) gave four positive colonies identified. The positive colonies obtained gave a plasmid pPMPYRG containing a genome DNA of approximately 4.7 kbp.

3. Determination of Base Sequence

The base sequence of the *Penicillium multicolor* pyrG gene in the translation region, which was determined by analyzing the base sequence of a DNA fragment of approximately 2.2 kbp, obtained by cleavage of the plasmid pPMPYRG containing the genome clone with KpnI, is shown by SEQ ID No. 14. The intron and the amino acid sequence of the pyrG protein were estimated from the base sequence of the translation region (SEQ ID No. 14 in the sequence listing). The amino acid sequence obtained (SEQ ID No. 15 in the sequence listing) was 88% homologous with that of *Penicillium chrysogenum* pyrG (Cantoral et al., Nucleic Acid Res. 16 (16): 8177, 1988).

4. Transformation

The orotidine-5'-phosphate decarboxylase-deficient strain of *Penicillium multicolor* IAM7153 (IAM7153ΔpyrG) obtained above was inoculated into 100 ml of a complete medium 2 (0.6% $NaNO_3$, 0.052% KCl, 0.052% $MgSO_4.7H_2O$, 0.152% $KH_2PO_4$, 0.15% Trace elements sol, 1% glucose, 0.1% uridine, 0.5% yeast extract, 0.5% casamino acids, 0.5% carboxymethylcellulose, pH 6.5) in a 500-ml Shaking flask, and incubated at 27° C. and 140 rpm for 4 to 6 days. The hypha was collected by filtration through a Tetoron mesh (230 mesh) and suspended in 40 ml of a protoplast solution (0.8 M NaCl, 10 mM $NaH_2PO_4$, 20 mM $CaCl_2$, 3.0 mg/ml Yatalase, 0.3 mg/ml Novozyme 234), and the mixture was shaken gently at 30° C. for 1 hour. The protoplast was collected by filtration through a Tetoron mesh, and obtained as sediment after centrifugation at 440×g for 5 minutes. The sediment was suspended in 10 ml of 0.8 M NaCl solution, and centrifuged at 440×g for 5 minutes for collection of the precipitate. The sediment was resuspended in 10 ml of 0.8 M NaCl and 50 mM $CaCl_2$ solution and centrifuged at 440×g for 5 minutes for collection of the sediment. The sediment was resuspended in a suitable amount of 0.8 M NaCl and 50 mM $CaCl_2$ solution, to give a protoplast solution.

Subsequently, 20 µg of the plasmid pPMPYRG containing a marker gene, orotidine-5'-phosphate decarboxylase gene (pyrG), and 12.5 µl of a PEG solution (25% PEG6000, 50 mM $CaCl_2$, 110 mM Tris-HCl, pH 7.5) were added to 50 µl of the protoplast solution, and the mixture was stirred and then left still on ice for 20 minutes. 0.5 ml of the PEG solution was then added thereto, and the mixture was agitated and then left still on ice for 5 minutes. 1 ml of 0.8 M NaCl and 50 mM $CaCl_2$ solution was added thereto and the mixture stirred. 0.75 ml of the liquid mixture was applied on 20 ml of a regeneration medium 2 containing 2% agar (0.6% $NaNO_3$, 0.152% $KH_2PO_4$, 0.052% KCl, 0.052% $MgSO_4.7H_2O$, 1% Glucose, 1.2 M Sorbitol, pH 6.5) and incubated at 27° C. for 5 to 8 days.

5. Southern Blotting Analysis of Transformant

The host and the eight transformants were inoculated on 100 ml of a YPM medium (1% yeast extract, 2% peptone, 2% maltose, pH 6.0) in 500-ml Shaking flask and incubated at 27° C. and 140 rpm for 6 days by shaking culture. The chromosomal DNA was prepared according to the method described in Hynes et al., (Mol. Cell. Biol. 3 (8): 1430-1439, 1983). After digestion with a restriction enzyme EcoRV, the products were subjected to agarose electrophoresis and blotting. The pyrG gene DNA fragment labelled with DIG-High Prime (manufactured by Roche) and the filter were hybridized at 42° C. overnight by using DIG Easy Hyb Granules (Roche), and then, the filter was washed with 2×SSC/0.1% SDS (room temperature) and 0.1×SSC/0.1% SDS (68° C.). The fragments were then detected with DIG Nucleic Acid Detection Kit (manufactured by Roche), showing that all transformants contained a pyrG gene introduced.

Example 5

Introduction of Diglycosidase Gene into *Penicillium multicolor*

For introduction of a XhoI-recognizing site into the downstream pyrG gene for preparation of the DNA fragment containing the pyrG gene of pPMPYRG by cleavage, a mutagenic primer was prepared.

```
Sense primer (pyrGF):
CGGGGTACCTTCTGGCTGG          SEQ ID No. 16

Antisense primer (pyrGXhoR):
GTTGGCTCGAGGGCTCTTAG         SEQ ID No. 17
```

PCR reaction was performed by using pPMPYRG as a template and also using the primers pyrGF and pyrGXhoR, to give a DNA fragment of approximately of 1.8 Kb. The DNA fragment of approximately 1.8 Kb obtained by digestion of the PCR-amplified fragment with XhoI and KpnI was ligated with the plasmid obtained by cleavage of pBluescript II KS(+) with XhoI and KpnI, to give a plasmid pPYRGKX. Determination of its base sequence revealed that there was a XhoI-recognizing site formed in the PPYRGKX insertion fragment and that there is no change in its internal sequence.

Analysis of the DNA fragment inserted into pBNDG obtained in Example 3 showed that the diglycosidase gene was present in a DNA fragment of approximately 2.5 Kb obtained by cleavage with SpeI and ClaI. The DNA fragment of approximately 2.5 Kb obtained by cleavage of pBNDG with SpeI and ClaI was inserted into and ligated with the SpeI-ClaI cleavage fragment of pBluescript II KS(+), to give pBNDG-SC. The plasmid obtained by cleavage of pBNDG-SC with XhoI and KpnI was ligated with a DNA fragment of approximately 1.9 Kb containing the pyrG gene obtained by cleavage of pPYRGKX with XhoI and KpnI, to give pBNDG-PYRG. pBNDGPYRG was cleaved with SpeI and KpnI; after agarose gel electrophoresis, a DNA fragment of approximately 4.3 Kb containing the diglycosidase gene and the pyrG gene are collected, and the DNA therein was extracted with a GeneClean III kit (manufactured by BIO 101, Inc.). The TSIΔpyrG strain was transformed with the DNA obtained by the method shown in Example 4, in the following manner:

The orotidine-5'-phosphate decarboxylase-deficient strain of *Penicillium multicolor* IAM7153 (IAM7153ΔpyrG) was inoculated into 100 ml of a complete medium 2 (0.6% NaNO$_3$, 0.052% KCl, 0.052% MgSO$_4$.7H$_2$O, 0.152% KH$_2$PO$_4$, 0.15% Trace-elements sol, 1% glucose, 0.1% uridine, 0.5% yeast extract, 0.5% casamino acids, 0.5% carboxymethylcellulose, pH 6.5) in a 500-ml Shaking flask, and incubated at 27° C. and 140 rpm for 4 to 6 days by shaking culture. The hypha was collected by filtration through a Tetoron mesh (230 mesh) and suspended in 40 ml of a protoplast solution (0.8 M NaCl, 10 mM NaH$_2$PO$_4$, 20 mM CaCl$_2$, 3.0 mg/ml Yatalase, 0.3 mg/ml Novozyme 234), and the mixture was shaken gently at 30° C. for 1 hour. The protoplast was collected by filtration through a Tetoron mesh, and obtained as a precipitate after centrifugation at 440×g for 5 minutes. The precipitate was suspended in 10 ml of 0.8 M NaCl solution, and the suspension was centrifuged at 440×g for 5 minutes for collection of the sediment. The sediment was resuspended in 10 ml of 0.8 M NaCl and 50 mM CaCl$_2$ solution and centrifuged at 440×g for 5 minutes for collection of the sediment. The sediment was suspended in a suitable amount of 0.8 M NaCl and 50 mM CaCl$_2$ solution, to give a protoplast solution.

Subsequently, 4 μg of DNA fragment containing the marker gene orotidine-5'-phosphate decarboxylase gene (pyrG) and the diglycosidase gene and 6.75 μl of a PEG solution (25% PEG6000, 50 mM CaCl$_2$, 10 mM Tris-HCl, pH 7.5) were added to 50 μl of the protoplast solution, and the mixture was stirred and then left still on ice for 15 minutes. Then, 0.5 ml of the PEG solution and 1 ml of 0.8 M NaCl and 50 mM CaCl$_2$ solution were added, and the mixture was stirred gently.

0.75 ml of the liquid mixture was applied on 20 ml of a regeneration medium 2 containing 2% agar (10 mM NaNO$_3$, 0.1% KH$_2$PO$_4$, 0.05% KCl, 0.05% MgSO$_4$.7H$_2$O, 1% Glucose, 1.2 M Sorbitol, pH 6.5) and incubated at 27° C. for 5 to 8 days. The colony formed was transferred onto a PDK agar medium (potato dextrose agar medium, 2% KCl) and incubated at 27° C. for 3 to 4 days. The microorganism grown was transferred into a preculture medium (2.0% wheat germ, 2.0% glucose, 0.3% Meast PIG (manufactured by Asahi Brewery Foods), 0.5% KH$_2$PO$_4$, pH 5.5) and precultured at 27° C. and 300 rpm for 4 days. The preculture solution was inoculated into a production culture medium (1.3% degreasing soybean, 2.7% Pharmamedia (TRADERS), 4.0% Amalty sirup (manufactured by To a Kasei), 2.0% KH$_2$PO$_4$, pH 5.5) at a concentration of 1%, and the mixture was cultured at 27° C. and 200 rpm for 7 days. The enzyme activity of the supernatant of the culture solution after completion of culture was determined (see Table 3). The amount of the diglycosidase produced by each of the transformants (TF1 to TF3) was in the range of 18.8 to 21.5 U/ml.

TABLE 3

| Microorganism | Diglycosidase | β-Glucosidase | β-Xylosidase |
| --- | --- | --- | --- |
| TF1 | 18.8 U/ml | 12.8 U/ml | 3.6 U/ml |
| TF2 | 20.5 U/ml | 14.3 U/ml | 4.3 U/ml |
| TF3 | 21.5 U/ml | 17.4 U/ml | 4.5 U/ml |
| IAM7153 Δ pyrG | 1.2 U/ml | 16.7 U/ml | 2.6 U/ml |

INDUSTRIAL APPLICABILITY

The novel diglycosidase according to the present invention, which is higher in safety, diglycosidase activity and heat resistance, and can be produced reliably by using a microorganism as the supply source, is applicable to various applications such as foods, medicines, and quasi drugs, in particular for strengthening or weakening the fragrance, colorant or physiologically active ingredient in foods.

SEQUENCE LISTING

<160> NUMBER OF SEQ ID NOS: 18

Figure 1:
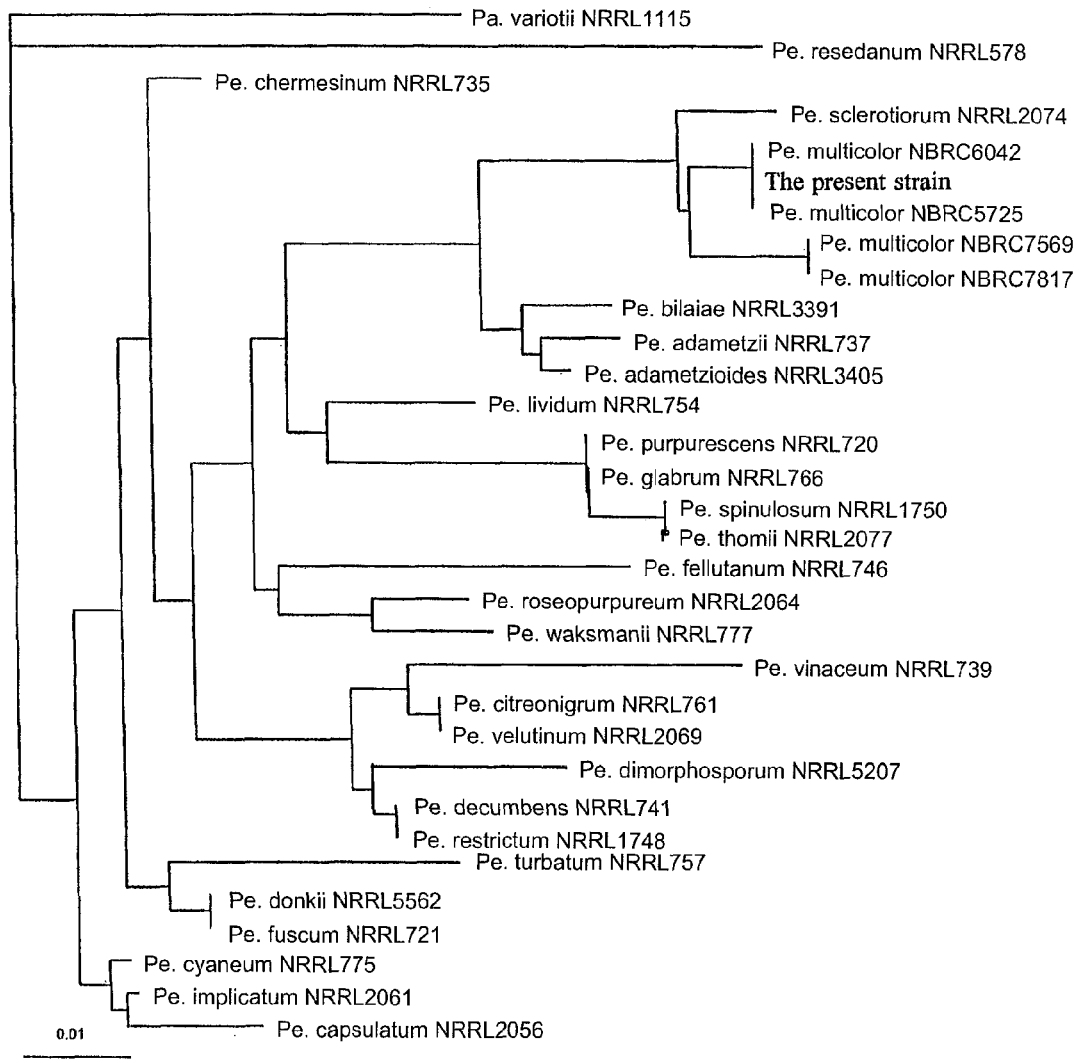
FIG. 1 is a chart showing the genealogical tree of Subgenus *Aspergilloides*.
Figure 2:
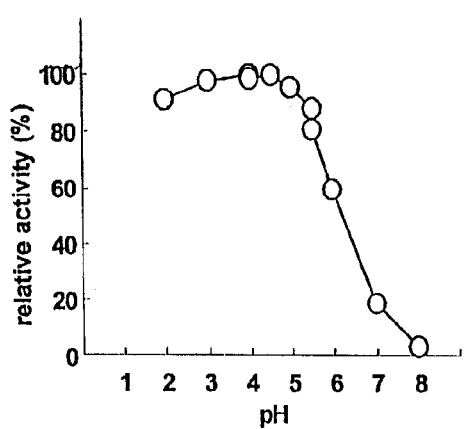
FIG. 2 is a graph showing the optimum pH.
Figure 3:
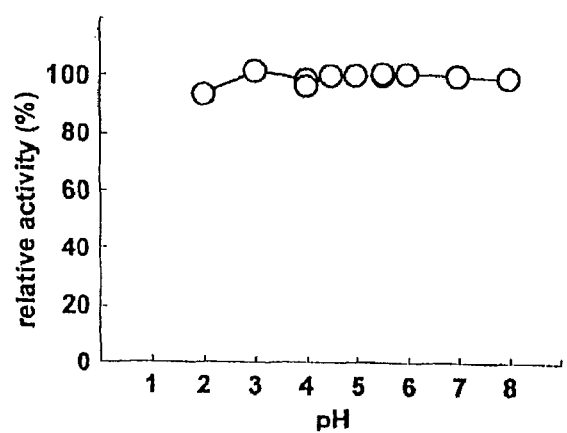
FIG. 3 is a graph showing the pH stability.
Figure 4:
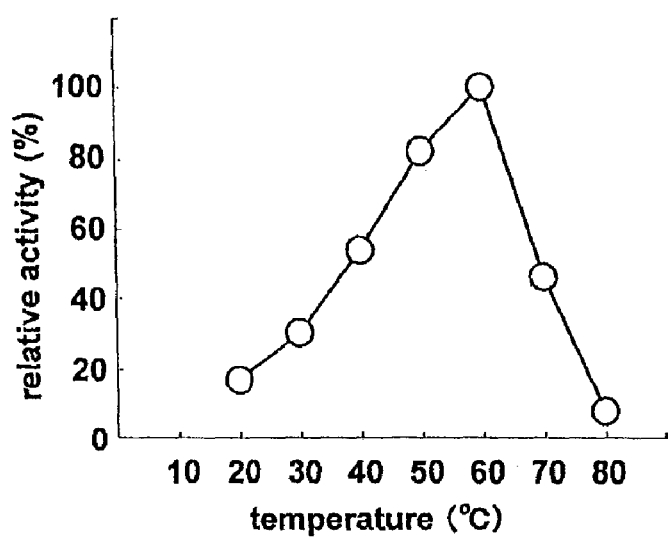
FIG. 4 is a graph showing the optimum temperature.
Figure 5:
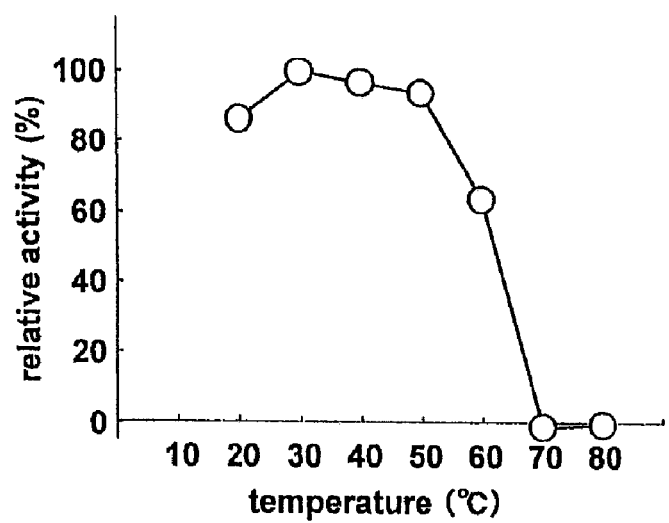
FIG. 5 is a graph showing the thermal stability.
Figure 6:
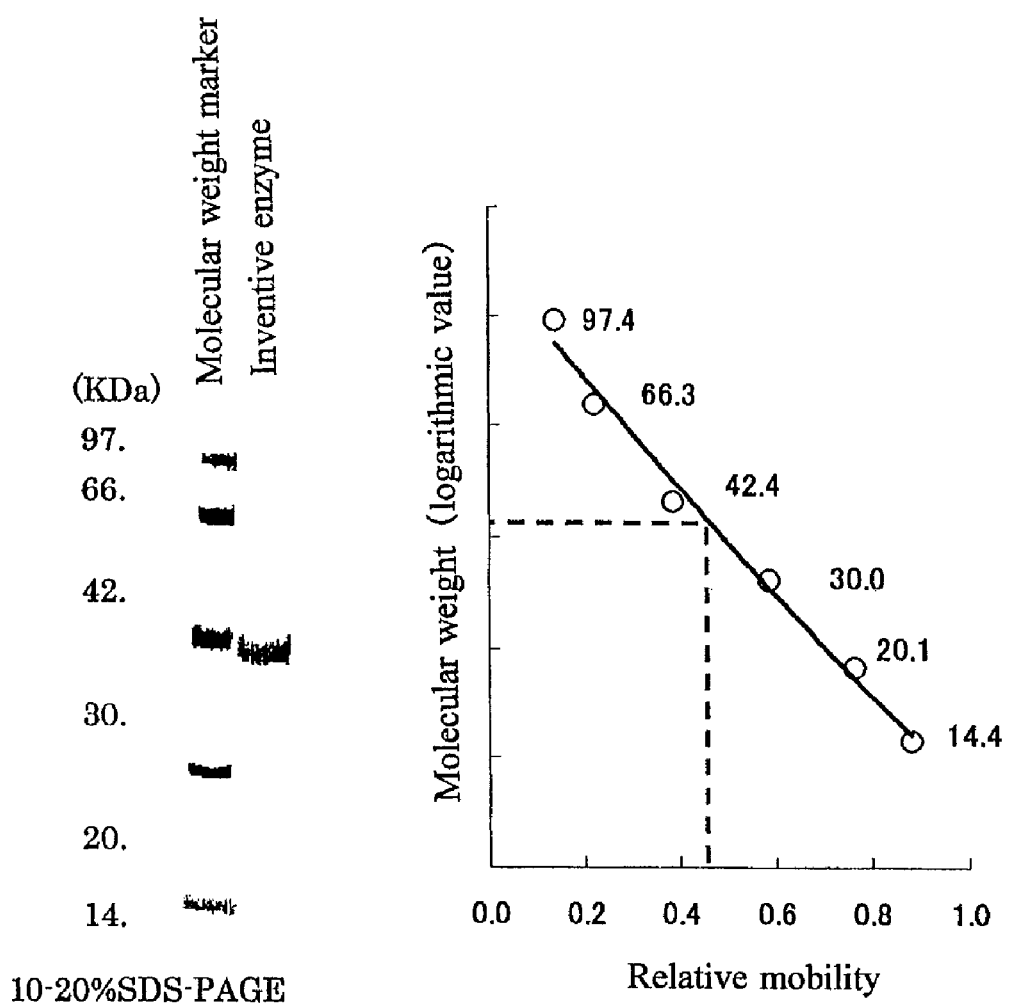
FIG. 6 is a graph showing the molecular weight measurement.
Figure 7:
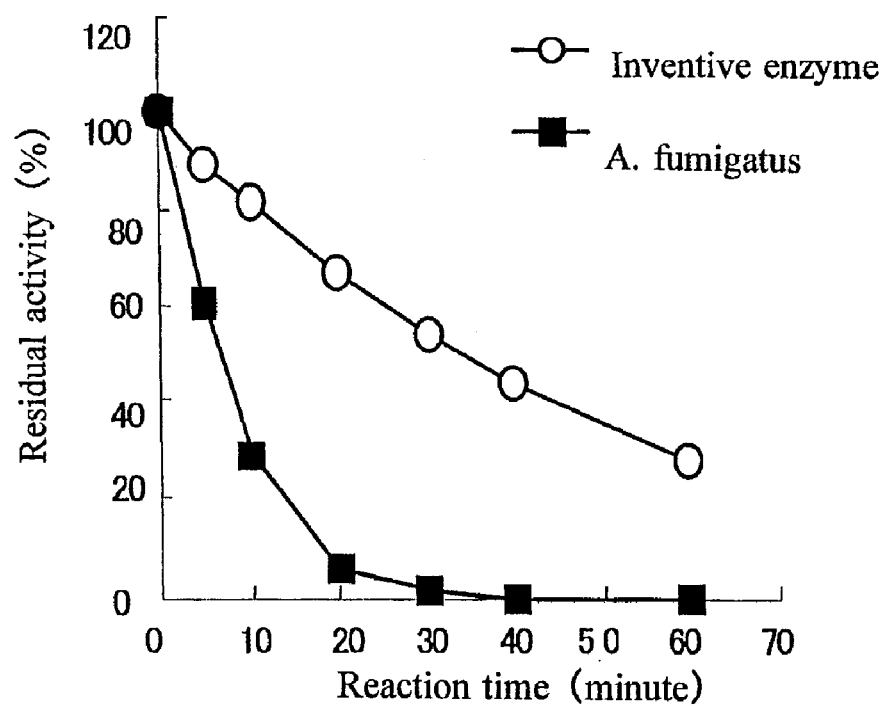
FIG. 7 is a graph comparing the thermal stability of the inventive enzyme with that of an Asp. fumigatus-derived enzyme.

<210> SEQ ID NO 1
<211> LENGTH: 15
<212> TYPE: PRT
<213> ORGANISM: Penicillium multicolor TS-5

<400> SEQUENCE: 1

Ser Thr Tyr Leu Asn Trp Thr Thr Phe Asn Ala Val Gly Ala Asn
1               5                   10                  15

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence : Primer
<220> FEATURE:
<221> NAME/KEY: misc_feature
<222> LOCATION: (3)..(3)
<223> OTHER INFORMATION: n stands for I
<220> FEATURE:
<221> NAME/KEY: misc_feature
<222> LOCATION: (9)..(9)
<223> OTHER INFORMATION: n stands for I

<400> SEQUENCE: 2
acntayytna aytggac                                                17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence : Primer
<220> FEATURE:
<221> NAME/KEY: misc_feature
<222> LOCATION: (6)..(6)
<223> OTHER INFORMATION: n stands for I
<220> FEATURE:
<221> NAME/KEY: misc_feature
<222> LOCATION: (9)..(9)
<223> OTHER INFORMATION: n stands for I

<400> SEQUENCE: 3
tggacnacnt tyaaygc                                                17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence : Primer
<220> FEATURE:
<221> NAME/KEY: misc_feature
<222> LOCATION: (9)..(9)
<223> OTHER INFORMATION: n stands for I
<220> FEATURE:
<221> NAME/KEY: misc_feature
<222> LOCATION: (12)..(12)
<223> OTHER INFORMATION: n stands for I
<220> FEATURE:
<221> NAME/KEY: misc_feature
<222> LOCATION: (15)..(15)
<223> OTHER INFORMATION: n stands for I

<400> SEQUENCE: 4
ttyaaygcng tnggngc                                                17

```
<210> SEQ ID NO 5
<211> LENGTH: 1101
<212> TYPE: DNA
<213> ORGANISM: Penicillium multicolor TS-5

<400> SEQUENCE: 5
agcacctatc tgaattggac aacgttcaat gctgtcggtg ccaacctagg cggctggctt      60
gtgcaagaat caaccattga caccacgtgg tgggctcagt actctggcgg tgctgtggac     120
gaatggggtc tttgtgccta ccaggggtct caatgtggac cggtccttga acgtcgatat     180
gccacttgga tcacgactgc agacattgat actctgggtg cggctggtgt caacgttctg     240
cgtattccca ctacatatgc ggcttgggtg aaggttccag ggtcgcaatt ataccatggc     300
aatcaacagt ccttcctggc tagcatatcg tcatatgcta tcaacaaata cggcatgcat     360
atcatcatcg acatacactc tcttcccggt ggtgtgaatg gcttcccatt tggtgaagcc     420
tatggacact acggctggtt taataaccag actgctctca atattccttg gaagctgtg      480 gatgcagcca tttcttttat ccaaaattcg aactctccac aatcatacac tttggcgcca     540
attaatgagc tgttgatgt tgaagatctt tccctgtttg aacgccgta ttgtcttacc       600 gatgatggcg ccgcgtactt agccagctac atgcatcaag tcattgctaa ggtggaggct     660
gttaacagtg agattccgat tatgttccaa ggcagcttca agggcgaagc ttactggtcc     720 tcaacccttta cgtccgacac gaacctggtg tttgacattc acaattacta tttcgaaggt    780
cgggcggcga gctcaaccaa cgtgacgcag cttatctgtg cggatgctgt cacctctgct    840
ggagatggaa aattcccgac gtttgttggc aatggtcta tccagacgca gattgccaac      900
aattttgcct cccgtgcgaa aatactagag actggccttg ctgcttggaa aaagtatacc     960
cgaggtagcg cttactggac caccaaattc acaggaaatg cgacagttga tggagagggc    1020
acccaggcag attattggaa ttatgaaaca ttcatcaact tgggatatac aaagtcaaca    1080
tctgcggctg taccatgcta g                                              1101

<210> SEQ ID NO 6
<211> LENGTH: 366
<212> TYPE: PRT
<213> ORGANISM: Penicillium multicolor TS-5

<400> SEQUENCE: 6

Ser Thr Tyr Leu Asn Trp Thr Thr Phe Asn Ala Val Gly Ala Asn Leu
1               5                   10                  15

Gly Gly Trp Leu Val Gln Glu Ser Thr Ile Asp Thr Thr Trp Trp Ala
            20                  25                  30

Gln Tyr Ser Gly Gly Ala Val Asp Glu Trp Gly Leu Cys Ala Tyr Gln
        35                  40                  45

Gly Ser Gln Cys Gly Pro Val Leu Glu Arg Arg Tyr Ala Thr Trp Ile
    50                  55                  60

Thr Thr Ala Asp Ile Asp Thr Leu Gly Ala Ala Gly Val Asn Val Leu
65                  70                  75                  80

Arg Ile Pro Thr Thr Tyr Ala Ala Trp Val Lys Val Pro Gly Ser Gln
                85                  90                  95

Leu Tyr His Gly Asn Gln Gln Ser Phe Leu Ala Ser Ile Ser Ser Tyr
            100                 105                 110

Ala Ile Asn Lys Tyr Gly Met His Ile Ile Ile Asp Ile His Ser Leu
        115                 120                 125

Pro Gly Gly Val Asn Gly Phe Pro Phe Gly Glu Ala Tyr Gly His Tyr
    130                 135                 140
```

```
Gly Trp Phe Asn Asn Gln Thr Ala Leu Lys Tyr Ser Leu Glu Ala Val
145                 150                 155                 160

Asp Ala Ala Ile Ser Phe Ile Gln Asn Ser Asn Ser Pro Gln Ser Tyr
            165                 170                 175

Thr Leu Ala Pro Ile Asn Glu Pro Val Asp Val Glu Asp Leu Ser Leu
            180                 185                 190

Phe Gly Thr Pro Tyr Cys Leu Thr Asp Asp Gly Ala Ala Tyr Leu Ala
            195                 200                 205

Ser Tyr Met His Gln Val Ile Ala Lys Val Glu Ala Val Asn Ser Glu
            210                 215                 220

Ile Pro Ile Met Phe Gln Gly Ser Phe Lys Gly Glu Ala Tyr Trp Ser
225                 230                 235                 240

Ser Thr Phe Thr Ser Asp Thr Asn Leu Val Phe Asp Ile His Asn Tyr
            245                 250                 255

Tyr Phe Glu Gly Arg Ala Ala Ser Ser Thr Asn Val Thr Gln Leu Ile
            260                 265                 270

Cys Ala Asp Ala Val Thr Ser Ala Gly Asp Gly Lys Phe Pro Thr Phe
            275                 280                 285

Val Gly Glu Trp Ser Ile Gln Thr Gln Ile Ala Asn Asn Phe Ala Ser
290                 295                 300

Arg Ala Lys Ile Leu Glu Thr Gly Leu Ala Ala Trp Lys Lys Tyr Thr
305                 310                 315                 320

Arg Gly Ser Ala Tyr Trp Thr Thr Lys Phe Thr Gly Asn Ala Thr Val
            325                 330                 335

Asp Gly Glu Gly Thr Gln Ala Asp Tyr Trp Asn Tyr Glu Thr Phe Ile
            340                 345                 350

Asn Leu Gly Tyr Thr Lys Ser Thr Ser Ala Ala Val Pro Cys
            355                 360                 365

<210> SEQ ID NO 7
<211> LENGTH: 1170
<212> TYPE: DNA
<213> ORGANISM: Penicillium multicolor TS-5
<220> FEATURE:
<221> NAME/KEY: CDS
<222> LOCATION: (1)..(1170)
<223> OTHER INFORMATION:
<220> FEATURE:
<221> NAME/KEY: mat_peptide
<222> LOCATION: (70)..(1167)
<223> OTHER INFORMATION:

<400> SEQUENCE: 7 atg aaa gcc atg aca tct gtt ata ttg cca ccg gta gca gcc ccc gcc    48
Met Lys Ala Met Thr Ser Val Ile Leu Pro Pro Val Ala Ala Pro Ala
        -20                 -15                 -10 ctt tgc ctc gct gcc gta tcc agc acc tat ctg aat tgg aca acg ttc    96
Leu Cys Leu Ala Ala Val Ser Ser Thr Tyr Leu Asn Trp Thr Thr Phe
    -5                  -1  1               5 aat gct gtc ggt gcc aac cta ggc ggc tgg ctt gtg caa gaa tca acc   144
Asn Ala Val Gly Ala Asn Leu Gly Gly Trp Leu Val Gln Glu Ser Thr
10                  15                  20                  25 att gac acc acg tgg tgg gct cag tac tct ggc ggt gct gtg gac gaa   192
Ile Asp Thr Thr Trp Trp Ala Gln Tyr Ser Gly Gly Ala Val Asp Glu
            30                  35                  40 tgg ggt ctt tgt gcc tac cag ggg tct caa tgt gga ccg gtc ctt gaa   240
Trp Gly Leu Cys Ala Tyr Gln Gly Ser Gln Cys Gly Pro Val Leu Glu
        45                  50                  55 cgt cga tat gcc act tgg atc acg act gca gac att gat act ctg ggt   288
Arg Arg Tyr Ala Thr Trp Ile Thr Thr Ala Asp Ile Asp Thr Leu Gly
```

```
                    60                    65                   70
gcg gct ggt gtc aac gtt ctg cgt att ccc act aca tat gcg gct tgg    336
Ala Ala Gly Val Asn Val Leu Arg Ile Pro Thr Thr Tyr Ala Ala Trp
 75                      80                  85 gtg aag gtt cca ggg tcg caa tta tac cat ggc aat caa cag tcc ttc    384
Val Lys Val Pro Gly Ser Gln Leu Tyr His Gly Asn Gln Gln Ser Phe
 90                  95                  100                 105 ctg gct agc ata tcg tca tat gct atc aac aaa tac ggc atg cat atc    432
Leu Ala Ser Ile Ser Ser Tyr Ala Ile Asn Lys Tyr Gly Met His Ile
                110                 115                 120 atc atc gac ata cac tct ctt ccc ggt ggt gtg aat ggc ttc cca ttt    480
Ile Ile Asp Ile His Ser Leu Pro Gly Gly Val Asn Gly Phe Pro Phe
            125                 130                 135 ggt gaa gcc tat gga cac tac ggc tgg ttt aat aac cag act gct ctc    528
Gly Glu Ala Tyr Gly His Tyr Gly Trp Phe Asn Asn Gln Thr Ala Leu
        140                 145                 150 aaa tat tcc ttg gaa gct gtg gat gca gcc att tct ttt atc caa aat    576
Lys Tyr Ser Leu Glu Ala Val Asp Ala Ala Ile Ser Phe Ile Gln Asn
    155                 160                 165 tcg aac tct cca caa tca tac act ttg gcg cca att aat gag cct gtt    624
Ser Asn Ser Pro Gln Ser Tyr Thr Leu Ala Pro Ile Asn Glu Pro Val
170                 175                 180                 185 gat gtt gaa gat ctt tcc ctg ttt gga acg ccg tat tgt ctt acc gat    672
Asp Val Glu Asp Leu Ser Leu Phe Gly Thr Pro Tyr Cys Leu Thr Asp
                190                 195                 200 gat ggc gcc gcg tac tta gcc agc tac atg cat caa gtc att gct aag    720
Asp Gly Ala Ala Tyr Leu Ala Ser Tyr Met His Gln Val Ile Ala Lys
            205                 210                 215 gtg gag gct gtt aac agt gag att ccg att atg ttc caa ggc agc ttc    768
Val Glu Ala Val Asn Ser Glu Ile Pro Ile Met Phe Gln Gly Ser Phe
        220                 225                 230 aag ggc gaa gct tac tgg tcc tca acc ttt acg tcc gac acg aac ctg    816
Lys Gly Glu Ala Tyr Trp Ser Ser Thr Phe Thr Ser Asp Thr Asn Leu
    235                 240                 245 gtg ttt gac att cac aat tac tat ttc gaa ggt cgg gcg gcg agc tca    864
Val Phe Asp Ile His Asn Tyr Tyr Phe Glu Gly Arg Ala Ala Ser Ser
250                 255                 260                 265 acc aac gtg acg cag ctt atc tgt gcg gat gct gtc acc tct gct gga    912
Thr Asn Val Thr Gln Leu Ile Cys Ala Asp Ala Val Thr Ser Ala Gly
                270                 275                 280 gat gga aaa ttc ccg acg ttt gtt ggc gaa tgg tct atc cag acg cag    960
Asp Gly Lys Phe Pro Thr Phe Val Gly Glu Trp Ser Ile Gln Thr Gln
            285                 290                 295 att gcc aac aat ttt gcc tcc cgt gcg aaa ata cta gag act ggc ctt   1008
Ile Ala Asn Asn Phe Ala Ser Arg Ala Lys Ile Leu Glu Thr Gly Leu
        300                 305                 310 gct gct tgg aaa aag tat acc cga ggt agc gct tac tgg acc acc aaa   1056
Ala Ala Trp Lys Lys Tyr Thr Arg Gly Ser Ala Tyr Trp Thr Thr Lys
    315                 320                 325 ttc aca gga aat gcg aca gtt gat gga gag ggc acc cag gca gat tat   1104
Phe Thr Gly Asn Ala Thr Val Asp Gly Glu Gly Thr Gln Ala Asp Tyr
330                 335                 340                 345 tgg aat tat gaa aca ttc atc aac ttg gga tat aca aag tca aca tct   1152
Trp Asn Tyr Glu Thr Phe Ile Asn Leu Gly Tyr Thr Lys Ser Thr Ser
                350                 355                 360 gcg gct gta cca tgc tag                                            1170
Ala Ala Val Pro Cys
            365
```

<210> SEQ ID NO 8

```
<211> LENGTH: 32
<212> TYPE: DNA
<213> ORGANISM: Artificial Sequence
<220> FEATURE:
<223> OTHER INFORMATION: Dsecription of Artificial Sequence : Primer

<400> SEQUENCE: 8
gcgccctgca ggatgtcbtc saagtcscam yt                                    32

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence : Primer

<400> SEQUENCE: 9
gcgccctgca ggcacatcga yatcctcwcy ga                                    32

<210> SEQ ID NO 10
<211> LENGTH: 32
<212> TYPE: DNA
<213> ORGANISM: Artificial Sequence
<220> FEATURE:
<223> OTHER INFORMATION: Dsecription of Artificial Sequence : Primer

<400> SEQUENCE: 10
gcgccctgca ggaagcacaa yttyytbatc tt                                    32

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence : Primer

<400> SEQUENCE: 11
gcgccctgca gggargaycg caarttcatc ga                                    32

<210> SEQ ID NO 12
<211> LENGTH: 32
<212> TYPE: DNA
<213> ORGANISM: Artificial Sequence
<220> FEATURE:
<223> OTHER INFORMATION: Dsecription of Artificial Sequence : Primer

<400> SEQUENCE: 12
gcgccctgca ggtgrtaytg ctghccvagc tt                                    32

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence : Primer
<220> FEATURE:
<221> NAME/KEY: misc_feature
<222> LOCATION: (24)..(24)
<223> OTHER INFORMATION: n stands for any base

<400> SEQUENCE: 13
gcgccctgca ggatratraa gtcngcaccb cg                                    32

<210> SEQ ID NO 14
<211> LENGTH: 902
<212> TYPE: DNA
<213> ORGANISM: Penicillium multicilor IAM7153
```

<400> SEQUENCE: 14

```
atgtcttcca agtcgcaatt gcccttcggt gctcgcgcaa ccagccaccc caacccgctg      60
gcccgaaagc tcttccaggt cgctgaggct aagaagagca atgtgaccgt gtccgcagat     120
gtcactacca ccaaggaact tcttgatctg gccgaccgtg agtgaacatt agacatcttt     180
cactctacga agaagcatga acctaacgcg acaatcaaat aggtcttggt ccctacatcg     240
ccgtcatcaa aacccatatc gatatcctct ccgactttgg tcccgagacc attagtggtc     300
tgaacgcctt ggccgcgaag cacaacttcc tcatcttcga agaccgcaag ttcatcgaca     360
ttggcaacac tgtgcagaag cagtaccaca atggcacctt gaagatctcc gaatgggccc     420
atattatcaa ctgcagcgtc ctccccggcg agggtatcgt tgaagctctg gcgcagaccg     480
cccaggccga cgacttcccc tacgcccgga gcgtggcct cttgattctg cagagatga      540
cctcaaaggg ctccctcgcg actggcgcct acacatctgc ctccgtggac tacgcacgca     600
agtacccaag cttcgtgctc ggcttcgttt ctacccggtc gctgactgag gtcccgtcca     660
gcgttaccgc tgccgacaac gaggatttta tcgtctttac taccggcgtt aacctgtcat     720
ccaagggaga taagcttggc cagcaatacc aaacgccaca gtcggctatt ggccgcggcg     780
cggactttat catcgcggga cgtggcatct acgctgctcc cgatcccgtt gaggctgcca     840
agcaatacca gcagcaagga tgggaagcct atctggctcg cgtgggcggt gccagccaat     900
aa                                                                    902
```

<210> SEQ ID NO 15
<211> LENGTH: 278
<212> TYPE: PRT
<213> ORGANISM: Penicillium multicolor IAM7153

<400> SEQUENCE: 15

```
Met Ser Ser Lys Ser Gln Leu Pro Phe Gly Ala Arg Ala Thr Ser His
  1               5                  10                  15

Pro Asn Pro Leu Ala Arg Lys Leu Phe Gln Val Ala Glu Ala Lys Lys
             20                  25                  30

Ser Asn Val Thr Val Ser Ala Asp Val Thr Thr Thr Lys Glu Leu Leu
         35                  40                  45

Asp Leu Ala Asp Arg Leu Gly Pro Tyr Ile Ala Val Ile Lys Thr His
     50                  55                  60

Ile Asp Ile Leu Ser Asp Phe Gly Pro Glu Thr Ile Ser Gly Leu Asn
 65                  70                  75                  80

Ala Leu Ala Ala Lys His Asn Phe Leu Ile Phe Glu Asp Arg Lys Phe
                 85                  90                  95

Ile Asp Ile Gly Asn Thr Val Gln Lys Gln Tyr His Asn Gly Thr Leu
            100                 105                 110

Lys Ile Ser Glu Trp Ala His Ile Ile Asn Cys Ser Val Leu Pro Gly
        115                 120                 125

Glu Gly Ile Val Glu Ala Leu Ala Gln Thr Ala Gln Ala Asp Asp Phe
    130                 135                 140

Pro Tyr Gly Pro Glu Arg Gly Leu Leu Ile Leu Ala Glu Met Thr Ser
145                 150                 155                 160

Lys Gly Ser Leu Ala Thr Gly Ala Tyr Thr Ser Ala Ser Val Asp Tyr
                165                 170                 175

Ala Arg Lys Tyr Pro Ser Phe Val Leu Gly Phe Val Ser Thr Arg Ser
            180                 185                 190

Leu Thr Glu Val Pro Ser Ser Val Thr Ala Ala Asp Asn Glu Asp Phe
        195                 200                 205
```

```
Ile Val Phe Thr Thr Gly Val Asn Leu Ser Ser Lys Gly Asp Lys Leu
    210                 215                 220

Gly Gln Gln Tyr Gln Thr Pro Gln Ser Ala Ile Gly Arg Gly Ala Asp
225                 230                 235                 240

Phe Ile Ile Ala Gly Arg Gly Ile Tyr Ala Ala Pro Asp Pro Val Glu
                245                 250                 255

Ala Ala Lys Gln Tyr Gln Gln Gln Gly Trp Glu Ala Tyr Leu Ala Arg
            260                 265                 270

Val Gly Gly Ala Ser Gln
            275

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence : Primer

<400> SEQUENCE: 16
cggggtacct tctggctgg                                                  19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence : Primer

<400> SEQUENCE: 17
gttggctcga gggctcttag                                                 20

<210> SEQ ID NO 18
<211> LENGTH: 321
<212> TYPE: DNA
<213> ORGANISM: Penicillium multicolor TS-5

<400> SEQUENCE: 18
agaccgatag cgaacaagta gagtgatcga aagatgaaaa gcactttgaa aagagagtta     60
aaaagcacgt gaaattgttg aaagggaagc gtttgcgatc agactcgccg acggggttca   120
gcctgccttc gggcaggtgt acttccccgc cggcgggcca gcgtcggttt gggcggccgg   180
tcaaaggccc tgggaatgta acgcctctcg gggcgtctta tagcccaggg tgtcatgcgg   240
cctgcccgga ccgaggaacg cgcttcggct cggacgctgg cataatggtc gtaaacgacc   300
cgtcttgaaa cacggaccaa g                                             321
```

What is claimed is:

1. An isolated protein, comprising:
   (a) the amino acid sequence of SEQ ID No. 6; or
   (b) an amino acid sequence 90% or more homologous with the amino acid sequence of SEQ ID No. 6 and having diglycosidase activity.

2. An isolated nucleic acid, comprising a sequence that encodes:
   (a) a protein including the amino acid sequence of SEQ ID No. 6; or
   (b) a protein including an amino acid sequence 90% or more homologous with the amino acid sequence of SEQ ID No. 6 and having diglycosidase activity.

3. A recombinant vector, comprising the isolated nucleic acid according to claim 2.

4. A transformed cell, comprising the recombinant vector according to claim 3.

5. A method of producing a diglycosidase, comprising culturing the transformed cell according to claim 4 in a medium, allowing production of the diglycosidase, and collecting the diglycosidase.

6. An isolated nucleic acid, comprising:
   (a) the sequence of SEQ ID No. 5; or
   (b) a sequence that hybridizes to the sequence of SEQ ID No. 5 under a stringent condition and encodes a protein having diglycosidase activity, wherein the stringent condition is 6×SSC and 0.5% SDS at 68° C., or 6×SSC, 0.5% SDS, and 50% formamide at 42° C.

7. A recombinant vector, comprising the isolated nucleic acid according to claim 6.

8. A transformed cell, comprising the recombinant vector according to claim 7.

9. A method of producing a diglycosidase, comprising culturing the transformed cell according to claim 8 in a medium, allowing production of the diglycosidase, and collecting the diglycosidase.

10. A novel isolated diglycosidase produced by a microorganism belonging to the genus *Penicillium*, having the following physical and chemical properties:
   (1) action and substrate specificity: it acts on a disaccharide glycoside, releasing the disaccharide sugar and the aglycone thereof;
   (2) optimum pH: around 4.5;
   (3) pH stability: it is stable at pH 4.0 to 8.0 under the processing condition of 37° C. for 30 minutes and retains its 80% or more of the activity even after processing at pH 4.0 or lower;
   (4) optimum temperature: around 60° C. in a sodium acetate-acetic acid buffer solution (pH 5.5);
   (5) thermal stability: it is stable at 50° C. or lower in a sodium acetate-acetic acid buffer solution (pH 5.5) and retains 45% of the activity even after processing at 60° C. for 40 minutes;
   (6) molecular weight: 40,000±5,000 Da based on SDS-PAGE measurement; and
   (7) isoelectric point (pI): about 4.3, wherein the microorganism is *Penicillium multicolor* TS-5 (FERM BP-10627).

11. A novel isolated diglycosidase produced by a microorganism belonging to the genus Penicillium, having the following physical and chemical properties:
   (1) action and substrate specificity: it acts on a disaccharide glycoside, releasing the disaccharide sugar and the aglycone thereof;
   (2) optimum pH: around 4.5;
   (3) pH stability: it is stable at pH 4.0 to 8.0 under the processing condition of 37° C. for 30 minutes and retains its 80% or more of the activity even after processing at pH 4.0 or lower;
   (4) optimum temperature: around 60° C. in a sodium acetate-acetic acid buffer solution (pH 5.5);
   (5) thermal stability: it is stable at 50° C. or lower in a sodium acetate-acetic acid buffer solution (pH 5.5) and retains 45% of the activity even after processing at 60° C. for 40 minutes;
   (6) molecular weight: 40,000±5,000 Da based on SDS-PAGE measurement; and
   (7) isoelectric point (pI): about 4.3, wherein the disaccharide glycoside is β-primeveroside and the microorganism is *Penicillium multicolor* TS-5 (FERM BP-10627).

12. A method of producing a diglycosidase, comprising culturing *Penicillium multicolor* TS-5 (FERM BP-10627) allowing production of the diglycosidase according to claim 10, and collecting the diglycosidase.

* * * * *